(12) United States Patent
Garrett

(10) Patent No.: US 9,504,661 B2
(45) Date of Patent: *Nov. 29, 2016

(54) DAPSONE TO TREAT ROSACEA

(71) Applicant: Allergan, Inc., Irvine, CA (US)

(72) Inventor: John S. Garrett, Fort Collins, CO (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,841

(22) Filed: Oct. 25, 2013

(65) Prior Publication Data
US 2014/0050680 A1 Feb. 20, 2014

Related U.S. Application Data

(62) Division of application No. 12/305,413, filed as application No. PCT/US2008/002549 on Feb. 27, 2008, now Pat. No. 8,586,010.

(51) Int. Cl.
| | | |
|---|---|---|
| *A61K 8/18* | (2006.01) | |
| *A61Q 17/04* | (2006.01) | |
| *A61K 31/415* | (2006.01) | |
| *A61K 31/135* | (2006.01) | |
| *A61K 31/10* | (2006.01) | |
| *A61K 31/145* | (2006.01) | |
| *A61K 8/46* | (2006.01) | |
| *A61K 9/00* | (2006.01) | |
| *A61K 9/06* | (2006.01) | |
| *A61K 47/32* | (2006.01) | |
| *A61Q 19/00* | (2006.01) | |
| *A61K 31/4164* | (2006.01) | |

(52) U.S. Cl.
CPC ............. *A61K 31/145* (2013.01); *A61K 8/46* (2013.01); *A61K 9/0048* (2013.01); *A61K 9/06* (2013.01); *A61K 31/4164* (2013.01); *A61K 47/32* (2013.01); *A61Q 19/00* (2013.01)

(58) Field of Classification Search
CPC ........ A61K 8/46; A61K 9/0048; A61K 9/06; A61K 9/0014; A61K 31/145; A61K 31/4164; A61K 31/10; A61Q 19/00
USPC .......................... 424/59; 514/386, 646, 709
See application file for complete search history.

(56) References Cited

U.S. PATENT DOCUMENTS

2007/0122435 A1* 5/2007 Osborne ....................... 424/401

OTHER PUBLICATIONS

Elewski et al. (A Comparison of 15% Azelaic Acid Gel and 0.75 % Metronidazole Gel in the Topical Treatment of Papulopustular Rosacea, Results of a Randomized Trial, Arch Dermatol (Nov. 2003), 139 (11): 1444-1450 [Downloaded from internet <URL: http://archderm.jamanetwork.com/article.aspx?articleid=479570 >], 7 pages).*

Nase (New rosacea treatments offer hope, Clinical Dermatology, Dermatology Times (Aug. 2005) 26 (8): 33, 40-41).*

(Continued)

*Primary Examiner* — Anna Pagonakis
*Assistant Examiner* — Miriam A Levin
(74) *Attorney, Agent, or Firm* — Laura L. Wine; Debra D. Condino

(57) ABSTRACT

The methods described herein provide treatment of rosacea using topical formulations of dapsone. The methods also provide treatment of rosacea with topical dapsone in combination with other active agents, including metronidazole. The methods avoid negative hematologic side effects, including hemolysis and hemolytic anemia, that are associated with oral administration of dapsone.

12 Claims, 11 Drawing Sheets

(56) References Cited

OTHER PUBLICATIONS

Wolf (Update on the Treatment of Rosacea, A Basic Guide to Current Approaches, Winter Clinical Dermatology Conference Proceedings, Supplement to Skin & Aging (May 2006), pp. 1-3).*
Dapsone (PubChem, dapsone, substance, SID 8149283, [Retrieved from internet <URL: http://pubchem.ncbi.nlm.nih.gov/summary/summary.cgi?sid=8149283&viewopt=Deposited >] [Downloaded: Jan. 9, 2015], 5 pages).*
Sulfacetamide (PubChem, sulfacetamide, substance, SID 17388721, [Retrieved from internet <URL: http://pubchem.ncbi.nlm.nih.gov/summary/summary.cgi?sid=17388721&viewopt=Deposited >], [Downloaded: Jan. 9, 2015], 5 pages ).*
A Phase II, Randomized Study of ACZONE™ (Dapsone) Gel, 5% for Papulopustular Rosacea, Clinical Trials.gov, first received Nov. 3, 2005; last updated May 27, 2011, ([Retrieved from internet <URL: https://clinicaltrials.gov/ct2/show/study/NCT00249782 >]), 3 pages.*
Bailey, Advances in Rosacea and Acne Vulgaris, The Dermatology Report, Summer 2008, vol. 2, No. 1, pp. 1-9 ([Retrieved from internet <URL: http://www.thedermatologyreport.com/derm/derm020104.html >]).*
Brown, Sonya K., et al., Acne Vulargis, Folliculitis, and Acne Rosacea, http://www.docstoc.com/docs/48078014/Acne-Vulgaris-Folliculitis-and-Acne-Rosacea; 5 pages.
Baldwin, Hilary, Clinically Diagnosing Acne Vularis vs Rosacea: What's the Difference?, http://www.medscape.org/viewarticle/588257, Mar. 27, 2013, p. 1.
Ceilley, Roger L., Advances in the topical treatment of acne and rosacea, Sep. 1, 2004, Journal of Drugs in Dermatology; Sep. 1, 2004, http://custom.buyitsellit.com/25365/Journal_of_Drugs_in_Dermatology_2004.pdf, 20 pages.
Frequently asked Questions, Mar. 27, 2013, http://www.rosacea.org/patients/faq.php, Frequently asked Questions from Rosacea.org (pp. 5-6).
Rosacea World Difference between Acne and Rosacea, http://www.rosaceaworld.com/difference-between-acne-and-rosacea, p. 1.
How is Rosacea different to Acne Vulgaris?, Mar. 27, 2013, http://stason.org/TULARC/health/rosacea-disorder/1-2-How-is-Rosacea-different-to-Acne-Vulgaris.html, 1 pg.

* cited by examiner

Mean Change From Baseline in Inflammatory Lesion Counts for Subjects
with ≥ 10 lesions (ITT)

Mean Percent Change From Baseline in Inflammatory Lesion Counts for Subjects with ≥ 10 lesions (ITT)

Mean Change From Baseline in Inflammatory Lesion Counts for Subjects with <20 Lesions Mean Percent Change From Baseline in Inflammatory Lesion Counts for Subjects with <20 Lesions Mean Change from Baseline in Inflammatory Lesion Counts for Subjects
With ≥ 20 Lesions Mean Percent Change from Baseline in Inflammatory Lesion Counts for
Subjects With ≥ 20 Lesions Summary of Investigator's Global Assessment Score
Baseline Lesion Count ≥ 10 lesions (ITT)

Summary of Investigator's Global Assessment Success Rate at Week 12
Baseline Lesion Count ≥ 10 lesions (ITT)

Summary of Investigator's Global Assessment
Baseline Lesion Count <20

Summary of Investigator's Global Assessment Success Rate for Subjects with ≥ 20 Inflammatory Lesions at Baseline

DAPSONE TO TREAT ROSACEA

CROSS REFERENCE TO RELATED APPLICATIONS

This is a divisional application of U.S. application Ser. No. 12/305,413, filed Aug. 5, 2010 which is a national stage application under 35 U.S.C. §371 of PCT patent application PCT/US2008/002549, filed on Feb. 27, 2008 which is hereby incorporated by reference in its entirety.

BACKGROUND OF THE INVENTION

Rosacea is a dermatological syndrome affecting approximately 14 million Americans. It is characterized by flushing of the skin, erythema, inflammatory papules and pustules, edema, telangiectasia, ocular symptoms and rhinophyma. To date, the etiology of rosacea is unknown and there is no clearly recognized cure (Bikowski and Goldman, 2004; Stone and Chodosh, 2004).

Four subtypes and one variation of rosacea have been defined. The subtypes are papulopustular rosacea, erythematotelangiectatic rosacea, phymatous rosacea, and ocular rosacea; the rosacea variation is granulomatous rosacea. Some patients may have features of more than one subtype simultaneously, and differences in severity occur within each subtype.

Management of rosacea is difficult because of the complexity of the syndrome and the sensitivity of rosacea-affected skin. Various therapies, including topical application of metronidazole, azelaic acid, sodium sulfacetamide/sulfur preparations, and antibiotics including erythromycin, clindamycin and tetracycline, are used in the management of rosacea with varying rates of success. Systemic therapy with oral tetracyclines, metronidazole and isotretinoin is also employed in the management of rosacea (Buechner, 2005). Dapsone antibiotic is effective for treating rosacea redness, facial flushing, papules and pustules when administered orally; however, the side effect profile makes the risk/benefit ratio too high for most rosacea sufferers (Nase, 2005).

What is needed are safe, effective treatments for the management of rosacea symptoms.

SUMMARY OF THE INVENTION

The invention is directed to the treatment of rosacea. The invention includes a method to treat rosacea by topically administering a pharmaceutical composition of dapsone and a pharmaceutically acceptable carrier to a patient. In preferred embodiments, the rosacea is papulopustular rosacea. In other embodiments, the rosacea is ocular rosacea. The invention is also directed to the treatment of ocular disorders. The invention includes a method to treat an ocular disease or disorder by topically administering a pharmaceutical composition of dapsone and a pharmaceutically acceptable carrier.

In some embodiments, the dapsone of the topical composition is entirely dissolved in the carrier; or partially dissolved and partially microparticulate; or may be present as an emulsion, suspension or colloid. In an entirely dissolved state, dapsone exists completely in solution in the solvent, with no solid dapsone present. If the dapsone is partially dissolved and partially microparticulate, a portion of the dapsone is present in solution and a portion of the dapsone is present in a solid form. A dapsone emulsion includes two immiscible, unblendable substances wherein one substance (the dispersed phase) is dispersed in the other (continuous phase). The dapsone can be part of the dispersed phase or part of the continuous phase of the emulsion. A dapsone suspension is a heterogeneous fluid containing solid particles of dapsone dispersed throughout a fluid. A dapsone colloid is a homogenous mixture of dispersed dapsone particles that are distributed evenly and stably throughout the continuous phase.

In certain embodiments, the pharmaceutical composition is a lotion, gel, ointment, cream, emulsion, suspension, spray, or cleanser. In a preferred embodiment, the pharmaceutical composition is a semisolid aqueous gel. The semisolid aqueous gel includes a thickening agent, water, a solvent, preservative, microparticulate dapsone, dissolved dapsone, and caustic material. In a preferred embodiment, the caustic material is a base agent. In a preferred embodiment, the composition exhibits an optimal balance between dissolved dapsone that is available to cross through the stratum corneum of the epidermis and be absorbed into the lower two-thirds of the pilosebaceous unit; and microparticulate dapsone that is retained in or above the stratum corneum to serve as a reservoir or to provide dapsone to the supracorneum zone, crossing the stratum corneum of the epidermis only minimally as a solid. The solid microparticulate dapsone reservoir is slowly dissolved in body fluids before it is delivered through the stratum corneum. In preferred embodiments, the dapsone makes up about 0.5% to 10% of the pharmaceutical composition. The microparticulate dapsone can be a crystalline precipitate or an amorphous precipitate. Antioxidants, fragrance, colorants, sunscreens, or combinations thereof may also be present in the topical composition. In preferred embodiments, the dapsone composition comprises about 5% dapsone, about 0.85% carbomer 980, about 25% diethylene glycol monoethyl ether (DGME), about 0.2% methylparaben, about 0.2% sodium hydroxide, and about 68.75% purified water.

The methods described herein include the treatment of papulopustular rosacea by applying the dapsone composition once or twice daily. In preferred methods the dapsone composition is applied twice daily. The methods additionally include the use of the dapsone pharmaceutical composition alone or in combination with other pharmaceutical compositions for rosacea, including topical and systemic treatments. The treatments are administered simultaneously or sequentially and include oral metronidazole, isotretinoin, tetracyclines including doxycycline, and topical metronidazole, azelaic acid, sodium sulfacetamide/sulfur preparations, and antibiotics including erythromycin, clindamycin and tetracycline. In some embodiments, the dapsone and other pharmaceutical are present in the same composition. In other embodiments, the dapsone and other pharmaceutical are present in separate compositions. In preferred embodiments, the dapsone pharmaceutical composition is applied topically in the AM and a separate metronidazole composition is applied topically in the PM, or vice versa.

In some embodiments, the patient has mild to severe papulopustular rosacea. In some embodiments, the patient has mild to moderate papulopustular rosacea. In other embodiments, the patient has moderate to severe papulopustular rosacea. In preferred embodiments, the rosacea is moderate to severe papulopustular rosacea. In some embodiments, the patient has at least ten papulopustular lesions before treatment, or preferably at least twenty papulopustular lesions before treatment. In a preferred embodiment, the number of papulopustular rosacea lesions is reduced by administering the dapsone composition topically. In some embodiments, the methods described herein result in blood plasma levels of dapsone of less than about 100 ng/mL.

In some embodiments, the patient has an Investigator's Global Assessment score of 3 or higher before treatment. In some embodiments, treatment results in a mean reduction of at least 13 papulopustular lesions. In some embodiments, treatment results in a mean reduction of at least 43% of the papulopustular lesions.

DETAILED DESCRIPTION OF THE INVENTION

Definitions

Figure 1:
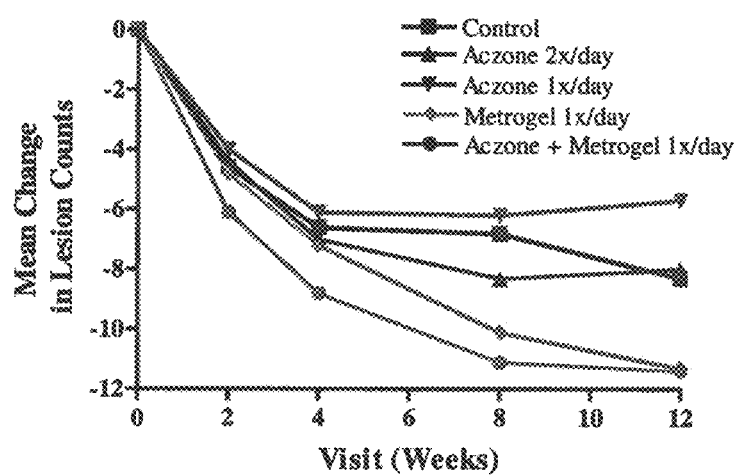
FIG. 1 shows the mean change from baseline in inflammatory lesion counts in the intent to treat (ITT) population having ≥10 inflammatory lesions (papules and/or pustules) above the mandibular line.

As used herein, "adverse event" means any adverse change in health or "side-effect" that occurs in a patient who is participating in a study while the patient is receiving treatment (dermatological composition or vehicle) or within a pre-specified period of time after their treatment has been completed.

As used herein, the term "colloid" refers to a homogenous mixture of two separate phases. The dispersed phase is made of tiny particles or droplets that are distributed evenly throughout the continuous phase. Colloids are stable mixtures and the dispersed phase generally does not settle out of the mixture.

As used herein, "dapsone" refers to the chemical compound dapsone having the chemical formula $C_{12}H_{12}N_2O_2S$ as well as bis(4-aminophenyl)sulfone, 4',4'-diaminodiphenyl sulfone and its hydrates, 4,4'-sulfonylbisbenzeneamine, 4,4'-sulfonyldianiline, diaphenylsulfone, dapsone analogs, and dapsone related compounds. "Dapsone analogs" refers to chemical compounds that have similar chemical structures and thus similar therapeutic potential to dapsone such as the substituted bis(4-aminophenyl)-sulfones. "Dapsone related compounds" refers to chemical compounds that have similar therapeutic potential, but are not as closely related by chemical structure to dapsone such as the substituted 2,4-diamino-5-benzylpyrimidines.

As used herein, the term "emulsion" describes a mixture of two immiscible, unblendable substances. The dispersed phase is dispersed in the continuous phase. For example, oil and water will form an emulsion when mixed together. In the compositions described herein, the oil phase may include but is not limited to fatty alcohols, acids, or esters such as cetyl palmitate, cetyl alcohol, stearyl alcohol, stearic acid, isopropyl stearate, glycerol stearate, mineral oil, white petrolatum, or other oils alone or in combination. Surfactants may be present in the emulsion to increase kinetic stability. Suitable emulsifiers that may be added to the compositions described herein include, but are not limited to, steareth 20, ceteth 20, sorbitan sesquioleate, sorbitan mono-oleate, propylene glycol stearate, sodium lauroyl sarcosinate, polysorbate 60, or combinations.

As used herein, "gel" refers to a colloid in a more solid form than a solution. A gel is also a jelly-like material formed by the coagulation of a colloidal liquid. Many gels have a fibrous matrix and fluid filled interstices. Gels are viscoelastic rather than simply viscous and can resist some mechanical stress without deformation.

As used herein, the term "mild rosacea" refers to papulopustular rosacea that includes mild erythema and several small papules/pustules.

As used herein, the term "moderate rosacea" refers to papulopustular rosacea that includes moderate erythema, with several small or large papules/pustules, and up to two nodules.

As used herein, the term "severe rosacea" refers to papulopustular rosacea that includes severe erythema and numerous small and/or large papules/pustules, and up to several nodules.

As used herein, the term "microparticulate" refers to any solid form of an active agent (dapsone) that is not dissolved in the topical composition. The microparticulate described herein may be in the form of flakes or crystals, and includes a precipitate of dapsone that results from the addition of water and the solvent or mixed solvent system. The microparticulate may comprise a crystalline precipitate or an amorphous precipitate.

As used herein, the term "ointment" means a semisolid, oil-based topical formulation. Examples of ointments include essentially non-aqueous mixtures of petrolatum, lanolin, polyethylene glycol, plant or animal oils, either hydrogenated or otherwise chemically modified. An ointment may also contain a solvent in which an active agent is either fully or partially dissolved.

As used herein, "pharmaceutically acceptable carrier" refers to a pharmaceutically acceptable solvent, suspending agent or vehicle for delivering an active agent to a patient. Pharmaceutically acceptable carriers are nontoxic to the cell or patient being exposed thereto at the dosages and concentrations employed. Often, the physiologically acceptable carrier is an aqueous pH buffered solution. Pharmaceutically acceptable carriers are readily available to the public. Suitable pharmaceutical carriers are described in Remington's Pharmaceutical Sciences, Mack Publishing Company, a standard reference text in this field. Pharmaceutically acceptable carriers may include antiadherents, binders, coatings, disintegrants, fillers, diluents, colorants, glidants, lubricants, and preservatives. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives. In a preferred embodiment, the pharmaceutically acceptable carrier includes ethoxydiglycol, also known as diethylene glycol monoethyl ether (DGME).

As used herein, the term "suspension" refers to a heterogeneous fluid containing solid particles dispersed throughout. The suspended phase or suspensoid is dispersed throughout the liquid in a moderately finely divided state, but not so finely divided as to acquire the stability of a colloidal system. The suspended phase will eventually settle out of the suspension.

The term "topical" or "topical surface" as used herein refers to the route of administration of a composition that involves direct application to the surface of the body being treated. Topical application may be to the skin, or to a mucous membrane, also called mucosa, lining all body passages that communicate with the exterior such as the respiratory, genitourinary, and alimentary tracts, and having cells and associated glands that secrete mucous. Topical application may be to mucous membranes of nose, mouth, eye, eyelid inner surface, etc., or may be to the surface of intact or compromised skin. Examples of topical application include application of gels or other semisolids to rub-on, solutions to spray, or liquids to be applied by an applicator, for example, as eye drops. Rinse-off application with washes, cleansers, or shampoos are also examples of topical application. Areas of the body especially suitable for application of the composition described herein include sites where rosacea symptoms may be present, including the skin of the face, scalp, ears and neck, and the eyes.

As used herein, the term "treat", "treatment", or "treating" refers to the reduction in number and/or severity of individual rosacea lesions, prevention of the development of rosacea symptoms including papulopustular lesions, or global improvement in the appearance of rosacea. Success of treatment may be indicated by a reduction from baseline in the raw number of papulopustular inflammatory lesions, by a percent reduction from baseline in papulopustular inflammatory lesions, or by an improvement from baseline in an Investigator's Global Assessment (IGA) score.

Methods of Treatment

The method of the invention described herein treats rosacea conditions, e.g., papulopustular, erythematotelangiectatic, phymatous, and ocular rosacea, by the topical application of a composition comprising dapsone and a pharmaceutically acceptable carrier. The composition is applied as needed to relieve rosacea symptoms. In some embodiments, the composition is applied every other day. In some embodiments, the composition is applied once daily. In some embodiments, the composition is applied twice daily. In certain embodiments, the composition is applied for at least one week, at least two weeks, at least three weeks, at least four weeks, at least five weeks, at least six weeks, at least seven weeks, at least eight weeks, at least nine weeks, at least ten weeks, at least eleven weeks, or at least twelve weeks. In some preferred embodiments, the composition is applied for at least twelve weeks. In other preferred embodiments, the composition is applied for at least six months, at least nine months, or at least a year.

Rosacea

Rosacea is a multifactorial chronic disorder that most often affects the skin of the central face including the nose, forehead, cheeks, and chin. Rosacea usually affects fair-skinned people 30 to 50 years of age who tend to blush or flush easily. Four subtypes of rosacea are described: papulopustular, erythematotelangiectatic, phymatous, and ocular (Wilkin et al. 2002; Bikowski and Goldman, 2004). Granulomatous rosacea is considered to be a part of the spectrum of rosacea, but is referred to as a variant, rather than a subtype, of rosacea (Khokhar and Khachemoune 2004).

Papulopustular rosacea is characterized by persistent central facial erythema with transient, central facial papules, pustules or lesions of both types. In preferred embodiments, mild to severe papulopustular rosacea is treated. In a more preferred embodiment, moderate to severe papulopustular rosacea is treated. Erythematotelangiectatic rosacea is characterized by flushing and persistent central facial erythema, with or without telangiectasia. Phymatous rosacea is characterized by thickening skin, irregular surface nodularities, and enlargement, which may occur on the nose, chin, forehead, cheeks or ears. Ocular rosacea is characterized by a foreign body sensation in the eye, burning or stinging, dryness, itching, ocular photosensitivity, blurred vision, telangiectasia of the sclera or other parts of the eye, or periorbital edema. Granulomatous rosacea is characterized by noninflammatory, hard, brown, yellow or red cutaneous papules; or nodules of uniform size (Bikowski and Goldman, 2004).

In a recent study of clinical patterns of rosacea, papules and pustules were found in 83% and 67% of a sample of 108 rosacea patients, respectively (Sibenge and Gawkrodger, 1992). In the papulopustular subtype of rosacea, patients typically present with persistent central facial erythema with transient papules or pustules or both. Symptoms of burning, stinging, and dry skin are common (Wilkin et al. 2002; Dahl 2004). Other symptoms include flushing, erythema, and telangiectasia. While the exact pathogenesis of rosacea is unknown, inflammatory and vascular components are believed to be important in its pathogenesis.

The methods of the invention described herein include treatment of papulopustular rosacea lesions. In certain embodiments, the treatment of rosacea lesions results in a decrease or reduction from the baseline number of lesions by at least 2 lesions, at least 3 lesions, at least 4 lesions, at least 5 lesions, at least 6 lesions, at least 7 lesions, at least 8 lesions, at least 9 lesions, at least 10 lesions, at least 11 lesions, at least 12 lesions, at least 13 lesions, at least 14 lesions, at least 15 lesions, at least 16 lesions, at least 17 lesions, at least 18 lesions, at least 19 lesions, at least 20 lesions, at least 30 lesions, at least 40 lesions, or more than 40 lesions. In certain embodiments, the treatment of rosacea lesions results in a percentage decrease or reduction of lesions from baseline of at least 20%, at least 25%, at least 30%, at least 35%, at least 40%, at least 45%, at least 50%, at least 55%, at least 60%, at least 65%, at least 70%, at least 75%, or more than 75%.

About half of all rosacea sufferers also have some involvement of the eyes, known as ocular rosacea (Starr and McDonald, 1969). Eye problems may precede the common skin-related rosacea symptoms though it more common for the skin symptoms to appear first (Borrie, 1953). Ocular rosacea symptoms include dry eyes or tearing, redness, burning, pain, a gritty feeling in the eye, scales and crusts on the eyelids, sensitivity to light and blurry vision (Jenkins 1979).

Blepharitis, which includes inflammation of eyelashes or lid margins, is commonly seen in ocular rosacea. Blepharitis often results in red, itchy, burning eyes and lashes as well as scales and crusts on the eyelids. Sties, which are infections of eyelash follicles, may be present. Ocular rosacea sufferers may also have chalazia or meibomitis, characterized by enlarged, inflamed or plugged meibomian glands (which normally lubricate the eyelids). Scleritis and episcleritis, which are inflammatory conditions of the white outer coating of the eye (sclera) and connective tissue between the conjunctiva and sclera (episclera) may also be present in ocular rosacea.

Keratitis and iritis, which are infections or inflammation of the cornea and iris, respectively, may also be present in patients with ocular rosacea. These conditions may result in severe eye pain, blurry vision, formation of pus, and sensitivity to light. In severe ocular rosacea, ulcers may be present at the border of the cornea and sclera. This corneal ulceration, if untreated, may lead to perforation of the eye, a potentially blinding complication.

Management of rosacea is difficult because of the complexity of the syndrome and the sensitivity of rosacea-affected skin. Various therapies, including topical application of metronidazole, azelaic acid, sodium sulfacetamide/sulfur preparations, and antibiotics including erythromycin, clindamycin and tetracycline, are used in the management of rosacea with varying rates of success. Systemic therapy with oral tetracyclines, metronidazole and isotretinoin is also employed in the management of rosacea (Buechner, 2005). Oral dapsone antibiotic is effective for treating rosacea redness, facial flushing, papules and pustules; however, the side effect profile makes the risk/benefit ratio too high for most rosacea sufferers (Nase, 2005).

Ocular Indications

In addition to ocular rosacea, other ocular diseases may be treated with the topical dapsone compositions of the present invention. These diseases may be associated with inflammation, infection or other pathologies and the ocular involvement may be a primary or secondary manifestation of the disease or disorder. These diseases and disorders include conjunctivitis; scleritis including nodular scleritis secondary to Sweet's syndrome; vasculitis including autoimmune vasculitis and retinal vasculitis of Eales' disease; uveitis including granulomatous uveitis and panuveitis; ocular cicatricial pemphigoid; ocular leprosy; ocular manifestations of arachnid envenomation, Behçet disease, linear IgA disease, relapsing polychondritis, peripheral keratitis, tuberculosis, Hodgkin lymphoma, non-Hodgkin lymphoma, T-cell lymphoma and Reiter's syndrome; tumors of the eyelids; erythema elevatum diutinum; eyelid manifestations of erosive lichen planus; and *pneumocystis carinii* choroiditis associated with AIDS. The topical dapsone compositions of the present invention may be particularly formulated for treatment of ocular conditions. These formulations will be known to those of skill in the art and include drops, gels, ointments, cleansers and other topical formulations.

Dapsone

Dapsone was first synthesized in 1908 and has been used medically as an antibiotic and an anti-inflammatory. Dapsone is a bis(4-aminophenyl)sulfone also known as 4',4'-diaminodiphenyl sulfone, 4,4'-sulfonylbisbenzeneamine, 4,4'-sulfonyldianiline, and diaphenylsulfone. Dapsone has been used orally for the treatment of acne (Ross, 1961).

Dapsone analogs and related compounds have been described in U.S. Pat. Nos. 4,829,058 and 4,912,112 to Seydel et al. The '058 patent discloses substituted bis(4-aminophenyl)sulfones useful for inhibiting growth of bacteria, mycobacteria, and plasmodia. Some of these compounds were also tested against dapsone for toxicity and anti-inflammatory activity. In the '112 patent, substituted 2,4-diamino-5-benzyl pyrimidines having antimicrobial activity particularly against mycobacteria are described. Some of these compounds were also tested against dapsone for toxicity (Coleman et al., 1996) and anti-inflammatory activity (Coleman et al., 1997). The teachings of these references in combination with subsequent publications showed that these analogs and related compounds have activity similar to dapsone and would be expected to have similar treatment efficacy.

Currently, use of oral dapsone is generally limited, as its use may be associated with hematologic side effects, including hemolysis and hemolytic anemia that are dose-dependent and occur more frequently with increasing dose (Zhu and Stiller 2001; Jollow et al., 1995). The mechanism of dapsone-related hemolysis and hemolytic anemia involves oxidative damage to red blood cells and is associated with the dapsone hydroxylamine metabolite (Prendiville et al., 1988).

Topical Dapsone Compositions

Topical dapsone formulations have been described in U.S. Pat. No. 5,733,572 to Unger et al., and U.S. Pat. Nos. 6,056,954; 6,056,955; 6,254,866; 6,248,324; and 6,277,399 to Fischetti et al. A topical composition including dapsone for acne treatment has been described in U.S. Pat. Nos. 5,863,560 and 6,060,085 to Osborne which are herein incorporated by reference in their entirety.

The topical compositions described herein include dapsone and a pharmaceutically acceptable carrier. The carriers described herein are media useful for topical delivery of dapsone and optionally any additional active agents. These media, which are preferably organic or organic/aqueous mixtures, may be formulated as eye drops, lotions, gels, ointments, creams, sprays, washes, cleansers, shampoos, roll-on or stick products, micro-emulsions, shake powders, aerosolized sprays or mousse, and bath additives. Additional pharmaceutical carriers will be known to those skilled in the art and this list should not be considered to be limiting.

The dapsone of the topical composition may be entirely dissolved in the carrier; partially dissolved and partially microparticulate; or may be present as an emulsion, suspension or colloid. In an entirely dissolved state, dapsone exists completely in solution in the solvent, with no solid dapsone present. If the dapsone is partially dissolved and partially microparticulate, a portion of the dapsone is present in solution and a portion of the dapsone is present in a solid form. A dapsone emulsion includes two immiscible, unblendable substances wherein one substance (the dispersed phase) is dispersed in the other (continuous phase). The dapsone can be part of the dispersed phase or part of the continuous phase of the emulsion. A dapsone suspension is a heterogeneous fluid containing solid particles of dapsone dispersed throughout a fluid. A dapsone colloid is a homogenous mixture of dispersed dapsone particles that are distributed evenly and stably throughout the continuous phase.

Pharmaceutical carriers are pharmaceutically acceptable media for delivering active agent(s) to a patient. Pharmaceutically acceptable carriers include solvents, suspending agents or other vehicles that are nontoxic to the patient being exposed thereto at the dosages and concentrations employed. Pharmaceutical carriers of the compositions described herein will solubilize dapsone and any additional active agent(s) in whole or in part. Excipients present in the pharmaceutically acceptable carrier may include antiadherents, binders, coatings, disintegrants, fillers, diluents, colorants, glidants, lubricants, and preservatives.

In some embodiments, the topical compositions include a pharmaceutical carrier, dapsone, and an additional active pharmaceutical agent or agents. As described above, these dual agent compositions may be formulated as lotions, gels, ointments, creams, sprays, washes, cleansers, shampoos, roll-on or stick products, micro-emulsions, shake powders, aerosolized sprays or mousse, and bath additives. The dapsone and additional active pharmaceutical agent(s) of the topical composition may be entirely dissolved; partially dissolved and partially microparticulate; or may be present as an emulsion, suspension or colloid as described above. Suitable additional active pharmaceutical agents are disclosed, e.g., in Physician's Desk Reference (PDR), Medical Economics Company (Montvale, N.J.), (53rd Ed.), 1999; Mayo Medical Center Formulary, Unabridged Version, Mayo Clinic (Rochester, Minn.), January 1998; Merck Index, An Encyclopedia of Chemicals, Drugs, and Biologicals, (11th Ed.), Merck & Co., Inc. (Rahway, N.J.), 1989; and references cited therein.

Additional active pharmaceutical agents include, but are not limited to, anti-inflammatory agents, keratolytics, anti-infectives and acidic compounds. Anti-inflammatory agents, including corticosteroids, relieve inflammation including swelling, itching, and redness of the skin. Keratolytics are agents that soften skin cells and ease the flaking and peeling process. Examples include salicylic acid and urea. Anti-infectives including antibiotics, antifungals and antiseptics combat bacteria, fungi, and parasites. Acidic compounds contain an organic acid group or are at least weakly acidic in an aqueous-based solution and include retinoic acid, azelaic acid and lactic acid. In preferred embodiments, the additional active pharmaceutical agent is metronidazole anti-infective.

In preferred embodiments, the topical compositions described herein include thickening agents or thickeners. These substances increase viscosity, stability and improve suspending capability when added to a mixture. Known thickeners include inorganic water thickeners, polymeric thickeners, additives that promote thickening via lamellar structuring of surfactants, organic crystalline thickeners, and mixtures thereof. Suitable polymer thickeners for use in the topical compositions include cationic thickeners, non-ionic thickeners and anionic thickeners. Useful thickeners are described in detail below.

In preferred embodiments, the topical compositions described herein include solvent systems comprising organic solvents. These carbon-containing liquids dissolve solids, liquids, or gaseous solutes to form a solution. Solvents are grouped into polar (hydrophilic) and non-polar (lipophilic) types. Useful solvents are described in detail below. In preferred embodiments, the solvent of the topical compositions is diethylene glycol monoethyl ether (DGME), also known as ethoxydiglycol. In preferred embodiments, the topical composition of dapsone is formulated as an eye-drop and the solvent of such eye-drop compositions comprises a non-irritating solvent, more preferably diethylene glycol monoethyl ether (DGME), even more preferably DGME sold under the trade name "Transcutol™", even more preferably DGME having a percent purity of greater than 99.5%, such as those sold under the name "Transcutol™ CG," "Transcutol™ P" and "Transcutol™ HP."

Preservatives, antioxidants, fragrances, colorants, sunscreens, thickeners, suspending agents, enhancers, binders, disintegrants, fillers, diluents, colorants, glidants, lubricants, and other additives required to achieve pharmaceutically or cosmetically acceptable properties of the topical compositions may also be included. Topical compositions are not limited to these components, since one skilled in the art will be aware of additional components useful in the formulation of topical compositions.

The present compositions can include an alkali, also known as a base agent or caustic agent. The amount of alkali can be adjusted to change pH values of the topical compositions. The pH adjustment of the compositions of the present invention can be carried out by means of inorganic bases such as sodium hydroxide and potassium hydroxide; and organic bases such as triethylamine, diisopropanolamine, and triethanolamine (trolamine) The compositions may have a pH of about 7, e.g. 7.2, or below about 7. In other embodiments, the compositions of the present invention can be adjusted to have a pH below about 6.0, more specifically below about 5.5, even more specifically between about 4.0 to about 5.5, even more specifically between about 4.2 to about 5.4, or 4.4 to about 5.2, or about 4.8±0.5.

Thickeners

Suitable thickeners for use in the topical compositions include non-ionic thickeners, cationic thickeners and anionic thickeners. Suitable non-ionic thickening agents include polyacrylamide polymers, crosslinked poly(N-vinylpyrrolidones), polysaccharides, natural or synthetic gums, polyvinylpyrrolidone and polyvinylalcohol. Specific examples of non-ionic thickening agents include methyl hydroxypropyl cellulose, xanthan gum, polysaccharide gum, hydroxylpropyl cellulose, hydroxylpropyl methyl cellulose, hydroxylethyl cellulose, polyalkylene glycols, and mixtures thereof. Suitable anionic thickening agents include acrylic acid/ethyl acrylate copolymers, carboxyvinyl polymers and crosslinked copolymers of alkyl vinyl ethers and maleic anhydride.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably, the gelling agent comprises between about 0.2% to about 4% by weight of the composition. More particularly, the preferred compositional weight percent range for "CARBOPOL®" is between about 0.5% to about 2%, while the preferred weight percent range for "NATROSOL®" and "KLUCEL®" is between about 0.5% to about 4%. The preferred compositional weight percent range for both "HYPAN®" and "STABILEZE®" is between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

Solvents

In some embodiments, the topical compositions described herein are fluid solvent or mixed-solvent systems. The solvent can be an organic solvent, for example the solvent can include diethyleneglycol monoethyl ether (DGME), N-methylpyrrolidone (NMP), N,N-dimethylformamide, N,N-dimethylacetamide (DMA), dimethylsulfoxide (DMSO), or any other substantially non-toxic solvent suitable for application to human skin, wherein the solvent has at least some water solubility. Combinations of any of these solvents can also be used. Additional examples of solvents include ethanol, propylene glycol, glycerol, diethyleneglycol, triethyleneglycol, polyethylene glycol, propylene carbonate, pyrrolidone, N-methylpyrrolidone, dimethylsulfoxide, triethanolamine, 1,4-butanediol, ethyl acetate, triacetin, diacetin, dimethyl isosorbide, and the like, alone or in combination.

Other solvents can be used in conjunction with water to form the liquid of the inventive method. These solvents include, but are not limited to: benzyl alcohol, denatured alcohol, methanol, isopropyl alcohol, propanol, acetone, chlorobutanol, methyl ethyl ketone, sorbitan monolaurate, sorbitan monooleate, sorbitan monopalmitate, butanol, butyl alcohol, diglycerides, dipropylene glycol, eugenol, diacetin, diethanolamine, monoacetin, monoglycerides, PEG vegetable oil, N,N-dimethylformamide, N-methyl formamide, N-methylacetamide, N,N-dimethylacetamide, or combinations thereof.

Glycol ethers are organic solvents that are moderately soluble to miscible with water and can be used as a solvent in formation of a composition used in the methods described herein. A glycol ether is an ether formed from at least one glycol and at least one lower alkyl alcohol. Preferably the glycol is selected from an alkylene glycol such as ethylene glycol, propylene glycol, and butylene glycol. The ether portion of the glycol ether is a radical of a lower alkyl alcohol such as a $C_1$ to $C_6$ alcohol. Preferably, the ether portion alcohol is selected from methyl alcohol, ethyl alcohol, propyl alcohol, isopropyl alcohol, butyl alcohol, and isobutyl alcohol.

Examples of glycol ethers under the classification of ethylene glycol ethers include ethylene glycol monopropyl ether (propoxyethanol), ethylene glycol monobutyl ether (butoxyethanol), diethylene glycol monoethyl ether (ethoxydiglycol, DGME), diethylene glycol monobutyl ether (butoxydiglycol), diethylene glycol monoisopropyl ether (isopropyldiglycol), and diethylene glycol monoisobutyl ether (isobutyl diglycol).

Glycol ethers under the classification of propylene glycol ethers include propylene glycol monomethyl ether, dipropylene glycol monomethyl ether (PPG-2 methyl ether), tripropylene glycol monomethyl ether (PPG-3 methyl ether), propylene glycol n-propyl ether, dipropylene glycol n-propyl ether (PPG-2 propyl ether), propylene glycol monobutyl ether, dipropylene glycol monobutyl ether (PPG-2 butyl ether), propylene glycol monoisobutyl ether, and dipropylene glycol dimethyl ether. In one embodiment of the invention the solvent is ethoxydiglycol. Additional suitable exemplary glycol ethers are disclosed, e.g., in Aldrich Handbook of Fine Chemicals, 2003-2004 (Milwaukee, Wis.).

In some embodiments, compositions of the invention have a glycol ether present in about 20 wt. % to about 40.0 wt. %. In some embodiments, compositions of the invention have a glycol ether present in about 20.0 wt. % to about 35.0 wt. %. In some embodiments, compositions of the invention have a glycol ether present in about 25.0 wt. % to about 40.0 wt. %. In yet another embodiment, compositions of the present invention have a glycol ether present in about 25.0 wt. % to about 35.0 wt. % of the composition. More specifically, compositions of the present invention have a glycol ether present in about 25.0 wt. % of the composition.
Additives Preservatives may also be used in the pharmaceutical composition and preferably comprise about 0.05% to 0.5% by weight of the total composition. The use of preservatives assures that if the product is microbially contaminated, the formulation will prevent or diminish microorganism growth. Some preservatives useful in the pharmaceutical composition include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sunscreens include methyl cinnamate. Moreover, BHA may be used as an antioxidant, as well as to protect ethoxydiglycol and/or dapsone from discoloration due to oxidation. An alternate antioxidant is BHT.
Preferred Formulations As described herein, rosacea is treated by topically applying a topical composition comprising dapsone. In some embodiments, the topical composition comprises dissolved dapsone. In preferred embodiments, the topical composition is a pharmaceutical carrier system that is an aqueous gel, wherein the composition exhibits an optimal balance between dissolved dapsone that is available to cross through the stratum corneum to become systemically available, and microparticulate dapsone that is retained above the stratum corneum to serve as a reservoir or to provide dapsone to the supracorneum zone, crossing the stratum corneum of the epidermis only minimally as a solid. The solid microparticulate dapsone reservoir is slowly dissolved in body fluids and then delivered through the stratum corneum. In some embodiments, the microparticulate dapsone is any solid form of dapsone that is added to a saturated solution of dapsone. In other embodiments, the microparticulate dapsone may be a precipitate formed by the addition of water to a solution containing a solvent and dapsone. The precipitate may comprise a crystalline precipitate or an amorphous precipitate.

Optimal balance is accomplished by having a gel carrier system in which microparticulate dapsone is formed in reproducible ratios with respect to the dissolved dapsone. For the composition to have a wide range of applicability, the microparticulate to dissolved dapsone ratio preferably should be no greater than five, at therapeutic levels of applied active dapsone.

A composition having a microparticulate to dissolved dapsone ratio of less than two may provide the greatest amount of pharmaceutical available for immediate partition out of the stratum corneum and into the viable epidermis. This should provide minimum reservoir capacity, and may not maintain sustained delivery or provide maximum activity in the supracorneum zone. A composition having a microparticulate to dissolved dapsone ratio of two or greater may have a reduced amount of drug available for immediate partition out of the stratum corneum and into the viable epidermis. This provides maximum reservoir capacity, maintains sustained delivery through the stratum corneum by slowly dissolving the dapsone in body fluids, and provides activity in the supracorneum zone. For the present invention, the ratio for microparticulate drug to dissolved drug should be no greater than 50, and preferably no greater than 10. More preferably, the ratio for microparticulate drug to dissolved drug should be no greater than 7 or no greater than 6. Most preferably, the ratio for microparticulate drug to dissolved drug should be about 5.5, 5.4, 5.3, 5.2, 5.1 or 5.0. In some embodiments, the ratio for microparticulate drug to dissolved drug should be no greater than 5. Drug delivery from the microparticulate/dissolved dapsone formulation may be optimized to provide higher levels of drug to the supracorneum zone, while maintaining the level of drug partitioning through the stratum corneum and into the viable epidermis, despite 10-fold increases in the amount of pharmaceutical applied to the topical surface.

The compositions of the present invention comprise semi-solid and gel-like vehicles that include a thickener, water, preservatives, active surfactants or emulsifiers, antioxidants, sunscreens, and a solvent or mixed solvent system. The solvent or mixed solvent system is important to the formation of the microparticulate to dissolved dapsone ratio. The formation of the microparticulate, however, should not interfere with the ability of the thickener or preservative systems to perform their functions.

In a preferred embodiment, the topical composition comprises a thickening agent; water; a high-boiling, nonionic organic solvent; a preservative; dapsone in a microparticulate and dissolved state; and a base solution. In one embodiment, the topical composition that is applied includes about 0.5% to 4.0% carbomer and about 0.5% to 10% of dapsone that exists in both a dissolved state and a microparticulate state. The dissolved dapsone has the capacity to cross the stratum corneum, whereas the microparticulate dapsone does not. Addition of an amine base, potassium hydroxide solution, or sodium hydroxide solution completes the formation of the gel. A preferred ratio of microparticulate to dissolved dapsone is approximately five, which includes 5.5, 5.4, 5.3, 5.2, 5.1 and 5.0.

In some embodiments, the topical composition comprises about 5% dapsone, about 4% dapsone, about 3% dapsone, about 2% dapsone, or about 1% dapsone. In other embodiments, the topical composition comprises between 0.5% and 5% dapsone. In still other embodiments, the topical composition comprises between 0.5% and 10% of dapsone. In another embodiment, the pharmaceutical composition comprises about 1% carbomer, about 80-90% water, about 10% ethoxydiglycol (DGME), about 0.2% methylparaben, about 0.3% to 3.0% dapsone including both microparticulate dapsone and dissolved dapsone, and about 2% caustic material. More particularly, the carbomer may include "CARBOPOL® 980" and the caustic material may include sodium hydroxide solution.

In another embodiment, the composition comprises dapsone and ethoxydiglycol (DGME), which allows for an optimized ratio of microparticulate drug to dissolved drug. This ratio determines the amount of drug delivered, compared to the amount of drug retained above the stratum corneum to function as a reservoir or for action in the supracorneum domain. The system of dapsone and ethoxydiglycol may include purified water combined with "CARBOPOL®" gelling polymer, methylparaben, propylparaben, titanium dioxide, BHA, and a caustic material to neutralize the "CARBOPOL®."

In a preferred embodiment, the composition comprises about 5% dapsone, about 0.85% carbomer 980, about 25% diethylene glycol monoethyl ether (DGME), about 0.2% methylparaben, about 0.2% sodium hydroxide; and about 68.75% purified water.

The relative percentages for each of the reagents used in the pharmaceutical composition may vary depending upon the desired strength of the target formulation, gel viscosity, and the desired ratio of microparticulate to dissolved dapsone. Unless otherwise designated, all reagents listed above are commonly known by one of ordinary skill in the art and are commercially available from pharmaceutical or cosmetic excipient suppliers.

Additional Agents for Combination Therapy

It is contemplated that the methods described herein may include the use of other topical formulations in combination with topical dapsone. There are a number of specific courses of treatment that can be carried out. In some embodiments, the dapsone topical formulation and other topical formulation are administered simultaneously. In other embodiments, the dapsone topical formulation and other topical formulation are administered sequentially. Over the course of treatment, the administration of one formulation can continue when the other is discontinued and vice versa.

It is further contemplated that the methods described herein may include the use of other active pharmaceutical ingredients in combination with dapsone in a single topical composition. In these embodiments, the dapsone and other active ingredient are administered simultaneously.

Other topical formulations and active agents contemplated to be employed in conjunction with topical dapsone include, but are not limited to, metronidazole, azelaic acid, sodium sulfacetamide/sulfur preparations, and antibiotics including erythromycin, clindamycin and tetracycline. In one combination regimen, dapsone is applied in the AM and metronidazole is applied in the PM. In another combination regimen, metronidazole is applied in the AM and dapsone is applied in the PM.

It is further contemplated that the methods described herein include the use of systemic rosacea therapy in combination with topical dapsone therapy. Contemplated systemic therapies for use in combination with topical dapsone therapy include, but are not limited to, oral metronidazole and isotretinoin, and tetracyclines including doxycycline.

In one specific embodiment of the invention, the dapsone composition can be co-administered with photochemotherapy with ultraviolet A (PUVA). In another specific embodiment of the invention, the dapsone composition can be co-administered with phototherapy with UVB. As used herein, "photochemotherapy with ultraviolet A (PUVA)" refers to a type of ultraviolet radiation treatment (phototherapy) used for severe skin diseases. PUVA is a combination treatment which consists of Psoralen (P) administration and then exposure of the skin to long wave ultraviolet radiation (UVA).

Dapsone Plasma Levels

An advantage of the methods described herein is that blood plasma levels of dapsone and metabolites including N-acetyl dapsone and N-hydroxylamine dapsone are greatly reduced in comparison to oral administration of dapsone. The methods described herein employing topical dapsone are contemplated to result in blood plasma levels of dapsone and metabolites including N-acetyl dapsone and N-hydroxylamine dapsone less than about 150 ng/mL, less than about 100 ng/mL, less than about 90 ng/mL, less than about 80 ng/mL, less than about 70 ng/mL, less than about 60 ng/mL, less than about 50 ng/mL, less than about 40 ng/mL, less than about 30 ng/mL, less than about 20 ng/mL, less than about 10 ng/mL, less than about 9 ng/mL, less than about 8 ng/mL, less than about 7 ng/mL, less than about 6 ng/mL, less than about 5 ng/mL, less than about 4 ng/mL, less than about 3 ng/mL, less than about 2 ng/mL, and less than about 1 ng/mL.

Methods for Preparing Dapsone Topical Compositions

Those skilled in the art will be familiar with formulation methods used in preparing topical solutions or suspensions, lotions, ointments, creams and other formulations described above.

In some embodiments of the invention, a composition having dissolved dapsone and microparticulate dapsone is generally prepared by completely dissolving dapsone in a solvent or solvent mixture; adding and adequately dispersing a polymeric thickener in water; and combining the dissolved dapsone with the dispersed polymeric thickener. Alternatively, water may be slowly added to the dissolved dapsone, followed by the addition of a polymeric thickener. Ethoxydiglycol (DGME) and 1-methyl-2 pyrolidone are preferred solvents for use in the topically applied composition.

In some embodiments of the invention, the composition having dissolved dapsone and microparticulate dapsone is prepared by first forming a liquid by combining an organic solvent and water, and then contacting dapsone in a microparticulate solid form with the liquid, such that the microparticulate solid dapsone form does not entirely dissolve in the liquid; and dissolving a thickener in the liquid at a concentration sufficient to form a gel. In another embodiment of the invention, the composition having dissolved dapsone and microparticulate dapsone is prepared by, prior to the step of contacting the microparticulate solid dapsone with the liquid, forming a solution of the dapsone in the liquid, wherein the dapsone is substantially completely dissolved in the liquid.

In a preferred embodiment, the method for preparing a topically applied composition having dissolved and microparticulate dapsone comprises the steps of forming a homogenous dispersion by stirring purified water vigorously enough to form a vortex and sifting gel polymer into the vortex formed in the water while continuing to stir; forming a pharmaceutical component by dissolving methyl paraben and/or propylparaben in ethoxydiglycol by mixing to form a solution, and mixing dapsone with the solution until the pharmaceutical is dissolved; mixing the pharmaceutical component with the homogenous dispersion to form a microparticulate dapsone dispersion; and adding a caustic material.

The order in which reagents are combined may be important, depending on the particular reagents necessary for the target mixture. For example, after a pharmaceutical such as dapsone is dissolved in a solvent such as ethoxydiglycol, water may be slowly added to the dapsone in the ethoxydiglycol solution, or the dapsone in ethoxydiglycol solution may be added to the water with mixing. Adding the dapsone in ethoxydiglycol solution to water may result in less polydispersity in the size of the microparticulates than adding water to the dapsone in ethoxydiglycol solutions. The carbomer is generally dispersed in the water component of the formulation, while the remaining ingredients will be dissolved or dispersed in whichever of the two components are best for dissolving or dispersing the ingredient. For example, it is suggested to dissolve methylparaben, propylparaben, and BHA in ethoxydiglycol. After the ethoxydiglycol component and water component are combined, neutralizer is added to formulate the gel.

As described below, a study was conducted using as test subjects 399 male and female subjects≥18 years of age. At baseline, the subjects had a diagnosis of papulopustular rosacea, with ≥10 inflammatory lesions (papules and/or pustules) above the mandibular line. There was an overall improvement from baseline in local symptom scores with treatment. While treatment showed efficacy for patients with ≥10 inflammatory lesions, improved results were shown for subjects who entered the study with ≥20 inflammatory papulopustular lesions. It was surprising that the treatment was more successful for a more severe form of the disease. Topical application of 5% dapsone is safe and well tolerated when used to treat subjects with papulopustular rosacea. Systemic levels of dapsone and its metabolites were low during the study with no evidence of increasing exposure over time. No subjects in the study demonstrated evidence of hemolysis or treatment related hematological adverse events.

The invention will be described by the following non-limiting example.

Example 1

Methods

A twelve week study was conducted in 399 male and female subjects≥18 years of age. At baseline, the subjects had a diagnosis of papulopustular rosacea, with ≥10 inflammatory lesions (papules and/or pustules) above the mandibular line. Each subject had an Investigator Global Assessment (IGA) score≥2, as defined in Table 1.

TABLE 1

Investigator Global Assessment of Disease Severity

| Score | Severity | Description |
| --- | --- | --- |
| 0 | Clear | No signs or symptoms present; at most, mild erythema |
| 1 | Almost Clear | Very mild erythema present. Very few small papules/pustules |
| 2 | Mild | Mild erythema. Several small papules/pustules |
| 3 | Moderate | Moderate erythema. Several small or large papules/pustules, and up to 2 nodules |
| 4 | Severe | Severe erythema. Numerous small and/or large papules/pustules, up to several nodules. |

The subjects were randomly assigned to one of the following five treatment groups:
1) Vehicle Control (VC), 2×/day (80 subjects).
2) Aczone™ Gel, 5%, 2×/day (84 subjects).
3) Aczone™ Gel, 5%, 1×/day (79 subjects).
4) MetroGel® (metronidazole gel), 1%, 1×/day (80 subjects).
5) Aczone™ Gel, 5% 1×/day+MetroGel® (metronidazole gel), 1%, 1×/day (76 subjects).

MetroGel® is a 1% gel formulation of metronidazole. Metronidazole has been used as a topical therapy for rosacea since its approval in 1988 and is effective in reducing inflammatory papules and pustules and producing overall improvement in rosacea symptoms (Bikowski and Goldman, 2004).

MetroGel® contained the active ingredient metronidazole (10 mg per gram). Inactive ingredients in MetroGel® included: betadex, edetate disodium, hydroxyethyl cellulose, methylparaben, niacinamide, phenoxyethanol, propylene glycol, propylparaben, and purified water.

Aczone™ Gel is a 5% gel formulation of dapsone. Aczone™ gel contained the active ingredient dapsone (50 mg per gram). Inactive ingredients in the Aczone™ gel included: carbomer 980, diethylene glycol monoethyl ether (DGME), methylparaben, sodium hydroxide, and purified water. The vehicle control (VC) contained only the inactive components carbomer 980, diethylene glycol monoethyl ether (DGME), methylparaben, propylparaben, sodium hydroxide, and purified water.

The Aczone™ (dapsone 5%) gel was prepared as follows:

A polymer thickener component was prepared by charging 66.95 grams of purified water to a vessel suitable to contain 100 grams of finished semisolid product, and 0.85 g of "CARBOPOL® 980" was slowly sifted into a vortex formed by rapidly stirring the purified water. When a homogeneous dispersion of "CARBOPOL® 980" and water was formed, stirring was reduced to minimize air entrapment. Next, an active pharmaceutical component was prepared by charging an appropriately sized container with 25 g of ethoxydiglycol, then 0.2 g of methylparaben were added to the ethoxydiglycol and mixed until all of the crystalline solid was dissolved. 5.0 g dapsone was added to the ethoxydiglycol and mixed until the drug was completely dissolved. The polymer thickener component was added to the pharmaceutical component with mixing, immediately resulting in the formation of crystalline microparticles. Once the dispersion was homogenous, 2.0 grams of a 10% w/w aqueous sodium hydroxide solution were added to neutralize the CARBOPOL® 980 and form the gel.

The application procedures for all treatment groups were the same. Subjects applied a thin film of the study treatment onto the entire face and rubbed gently until it completely disappeared, after first washing the face with a standard cleanser. For twice-daily regimens, applications occurred once in the morning (AM) and once in the evening (PM). For once-daily regimens, applications occurred in the evening (PM). For the combination regimen, dapsone was applied in the AM and MetroGel® was applied in the PM.

Efficacy assessments included monitoring inflammatory lesion counts, Investigator Global Assessment (IGA) scores, erythema scores, and telangiectasia scores. Plasma dapsone concentrations were measured to assess systemic exposure to the study treatment. Safety was evaluated by monitoring adverse events, hematology and serum chemistry parameters, concomitant medications, vital signs, and local symptoms (dryness, itching, stinging, and burning).

Success rates, based on changes from baseline lesion counts and on the 5-point IGA, are direct indications of treatment response, and have been used in recent studies of other rosacea therapies (Wilkin et al., 2004; Thiboutot et al., 2003). Both of these endpoints are considered important and clinically relevant in evaluating the efficacy of treatments for rosacea. Erythema and telangiectasia are signs of rosacea that were evaluated according to standardized 4-point scales, and treatment-induced changes in these signs were considered to be clinically meaningful to subjects. Subjects were followed for 7 days after stopping treatment to monitor any ongoing adverse events.

Results

Inflammatory Lesion Counts.

The change from baseline in inflammatory lesion counts, percent change from baseline in inflammatory lesion counts, and lesion counts over time were summarized by N, mean, standard deviation, median, minimum, and maximum. Summaries were provided separately for each treatment group and study visit. In addition, 95% confidence intervals were provided for each treatment group and for the difference between vehicle control (VC) and each active treatment group.

The change from baseline in inflammatory lesion counts for each study visit was calculated by subtracting the baseline inflammatory lesion count from the post baseline study visit lesion counts for each subject. The percent change from baseline in inflammatory lesion counts was calculated by dividing the baseline inflammatory lesion count into the change from baseline in inflammatory lesion counts and then multiplying by 100 for each subject at each study visit.

At baseline, the mean inflammatory lesion count for all treatment groups was 21.6. FIG. 1 shows the mean change from baseline in inflammatory lesion counts in the intent to treat (ITT) population having ≥10 inflammatory lesions (papules and/or pustules) above the mandibular line. All study treatment groups experienced a mean decrease from baseline in lesion counts. Squares, vehicle control; triangles, Aczone™ (dapsone 5%) 2×/day; inverted triangles, Aczone™ (dapsone 5%) 1×/day; diamonds, MetroGel® (metronidazole 1%) 1×/day; circles, Aczone™ 1×/day+ MetroGel® 1×/day. At Week 12, subjects treated with MetroGel® alone or dapsone+MetroGel® experienced the largest mean decreases from baseline (−11.3 and −11.4 lesions, respectively) while subjects in the dapsone 1×/day group experienced the least mean decrease from baseline (−5.7 lesions from baseline). The mean change from baseline in the dapsone 2×/day group (−8.0 lesions) was higher than the dapsone 1×/day group, but similar to the VC group (−8.3 lesions), which was observed to decrease the number of inflammatory lesions.

A review of historical results for other approved therapies shows that the mean changes from baseline in lesion count for the dapsone 2×/day group was close to that of other approved products for rosacea, including Finacea® (azelaic acid) Gel, 15%, Oracea® (doxycycline) 40 mg capsules, and the active comparator in this study, MetroGel® (metronidazole), 1.0%. The changes from baseline in inflammatory lesion counts for Finacea® were reported as −10.7 and −8.9 (differences of 3.6 and 2.5 lesions in favor of active treatment over vehicle) (Finacea® package insert, 2005). For Oracea®, the changes from baseline in lesion counts were −11.8 and −9.5 (differences of 5.9 and 5.2 lesions in favor of active treatment over vehicle) (Oracea® package insert, 2006). Historically, subjects treated with the 1% strength of MetroGel® once-daily demonstrated a reduction in lesion count from baseline of −9.4 lesions, with a difference of 5.6 lesions over vehicle (MetroGel® package insert, 2005). The historical response for MetroGel® was less than the response observed in this study (−11.3 lesion decrease from baseline), which is most likely due to differences in study conditions and the fewer numbers of subjects enrolled in this study. In the intent-to-treat (ITT) analysis, treatment with the combination of MetroGel® and dapsone was not different from treatment with MetroGel® alone by Week 12 in terms of lesion count reduction.

Figure 2:
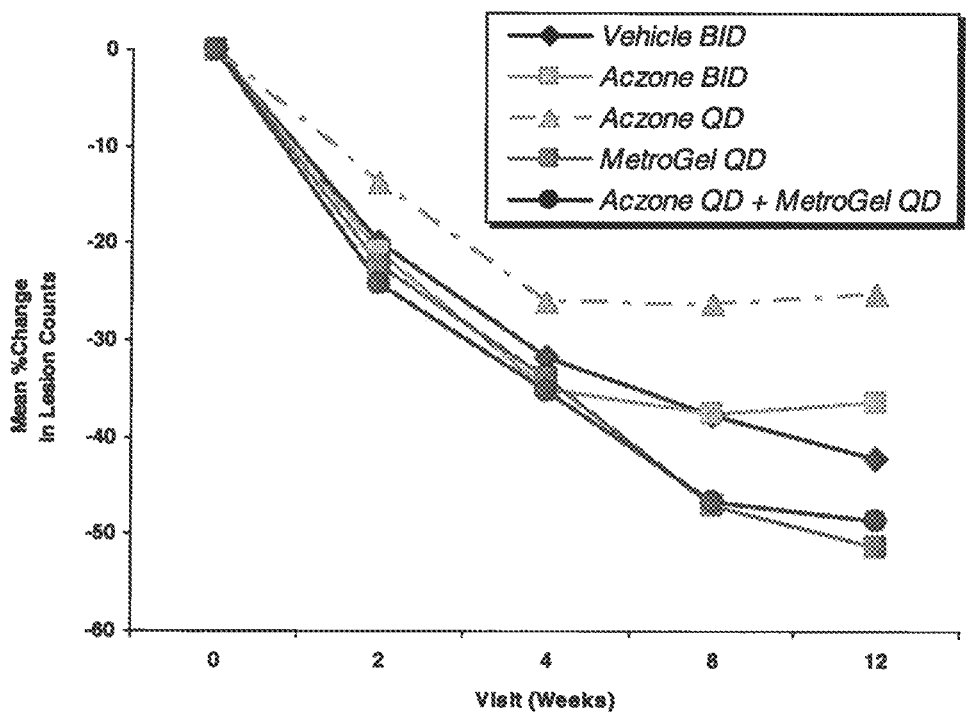
FIG. 2 shows the mean percent change from baseline in inflammatory lesion counts in the ITT population having ≥10 lesions (ITT).

FIG. 2 shows the mean percent change from baseline in inflammatory lesion counts in the intent to treat (ITT) population having ≥10 inflammatory lesions (papules and/or pustules) above the mandibular line. All study treatment groups experienced a mean percent decrease from baseline in lesion counts. Diamonds, vehicle control; light squares, Aczone™ (dapsone 5%) 2×/day; triangles, Aczone™ (dapsone 5%) 1×/day; dark squares, MetroGel® (metronidazole 1%) 1×/day; circles, Aczone™ 1×/day+MetroGel® 1×/day.

Subgroup Analysis: Subjects with <20 Lesions.

Figure 3:
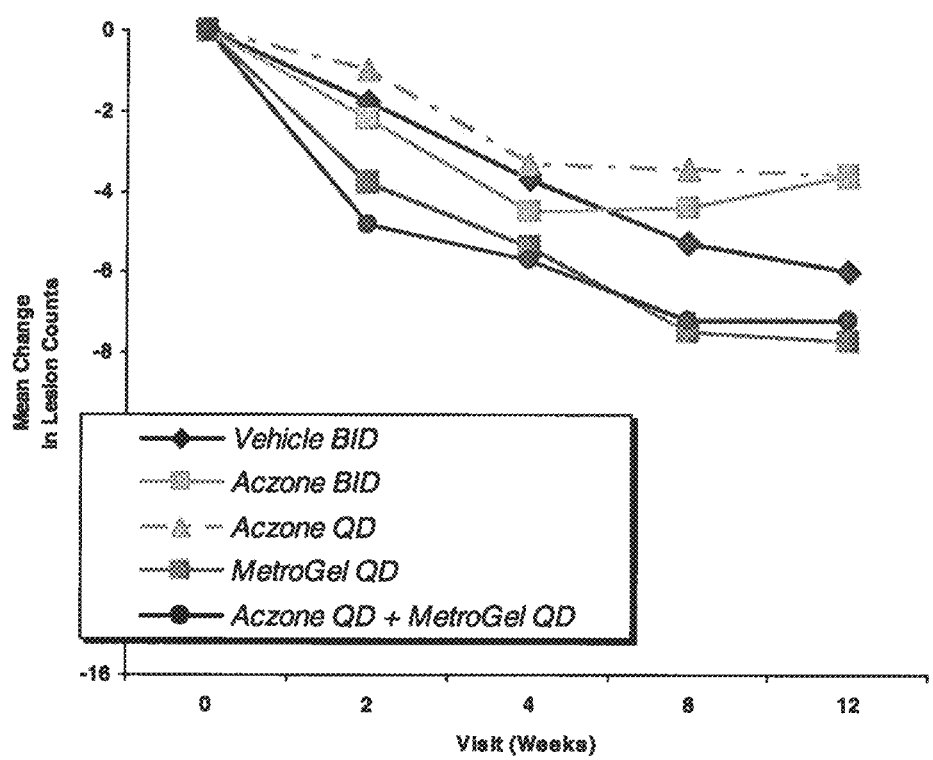
FIG. 3 shows mean change from baseline in inflammatory lesion counts for subjects with <20 lesions.

The subgroup of subjects with <20 lesions at baseline was analyzed independently of the ITT group. For this subgroup, the baseline mean inflammatory lesion count ranged from 13.6 lesions to 14.3 lesions across treatment groups, with an overall mean of 14.0 lesions. FIG. 3 depicts the mean change from baseline in lesion counts for this subgroup of subjects with <20 lesions at baseline. Diamonds, vehicle control; light squares, Aczone™ (dapsone 5%) 2×/day; triangles, Aczone™ (dapsone 5%) 2×/day; dark squares, MetroGel® (metronidazole 1%) 1×/day; circles, Aczone™ 1×/day+ MetroGel® 1×/day. Subjects in all treatment groups experienced a mean decrease from baseline in inflammatory lesion count. In this subgroup at week 12, the MetroGel® alone 1×/day experienced a mean decrease of −7.7 lesions; the dapsone+MetroGel® group experienced a mean decrease of −7.2 lesions; the vehicle control (VC) experienced a mean decrease of −6.0 lesions; and the dapsone 2×/day and dapsone 1×/day groups experienced a mean decrease of −3.6 lesions.

Figure 4:
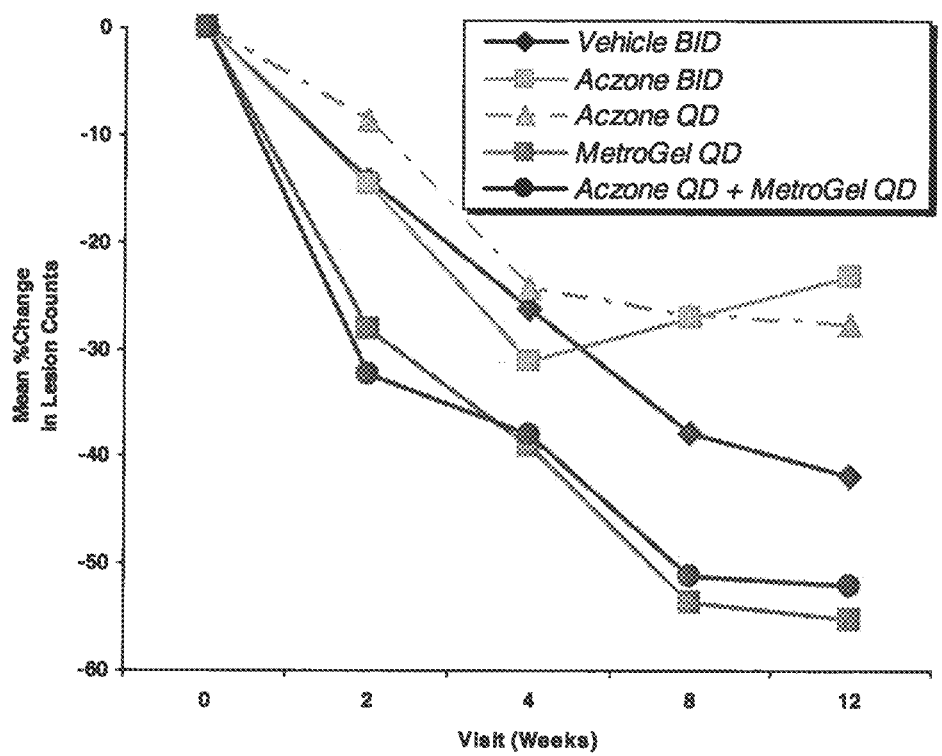
FIG. 4 shows mean percent change from baseline in inflammatory lesion counts for subjects with <20 lesions.

FIG. 4 shows the mean percent change from baseline in inflammatory lesion counts in the subgroup population having <20 inflammatory lesions (papules and/or pustules) above the mandibular line. All study treatment groups experienced a mean percent decrease from baseline in lesion counts. Diamonds, vehicle control; light squares, Aczone™ (dapsone 5%) 2×/day; triangles, Aczone™ (dapsone 5%) 1×/day; dark squares, MetroGel® (metronidazole 1%) 1×/day; circles, Aczone™ 1×/day+MetroGel® 1×/day. At Week 12, subjects treated with MetroGel® (metronidazole 1%) 1×/day or Aczone™ 1×/day+MetroGel® 1×/day experienced the largest mean percent decreases from baseline (55.3% and 52.0% mean reductions in lesions, respectively), while the vehicle control group experienced a 41.9% mean reduction in lesions. The dapsone 1×/day group experienced a 27.7% mean reduction in lesions and the dapsone 2×/day experienced a 23.3% mean reduction in lesions.

Subgroup Analysis: Subjects with ≥20 Lesions.

The subgroup of subjects with ≥20 lesions at baseline was analyzed independently of the ITT group. The cut-off of 20 lesions was chosen as the number which most closely approximated the baseline mean lesion count in subjects who entered the study with a baseline IGA in the moderate or severe categories. The size of this subgroup was relatively large (42% of the ITT population).

Figure 5:
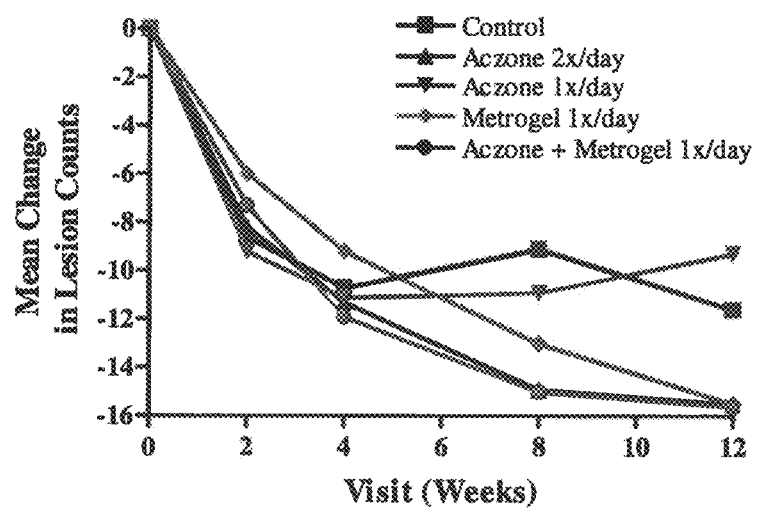
FIG. 5 shows the mean change from baseline in lesion counts for the subgroup of subjects with ≥20 lesions.

For this subgroup, the baseline mean inflammatory lesion count ranged from 28.4 lesions to 33.8 lesions across treatment groups, with an overall mean of 32.1 lesions. FIG. 5 depicts the mean change from baseline in lesion counts for this subgroup of subjects with ≥20 lesions at baseline. Squares, vehicle control; triangles, Aczone™ (dapsone 5%) 2×/day; inverted triangles, Aczone™ (dapsone 5%) 1×/day; diamonds, MetroGel® (metronidazole 1%) 1×/day; circles, Aczone™ 1×/day+MetroGel® 1×/day. Subjects in all treatment groups experienced a mean decrease from baseline in inflammatory lesion count that was higher than the overall mean decrease for the ITT population. In this subgroup, the dapsone 2×/day, MetroGel®, and dapsone+MetroGel® groups experienced the highest mean decreases by Week 12 (−15.5, −15.5, and −15.6 lesions respectively). The dapsone 1×/day and VC groups, respectively, experienced mean decreases of −9.3 and −11.6 lesions. Comparing the dapsone 2×/day and Vehicle Control groups, there was a 3.9 lesion difference in the mean decrease from baseline in favor of dapsone, similar to the differences between active and vehicle for other approved treatments (as described above).

Figure 6:
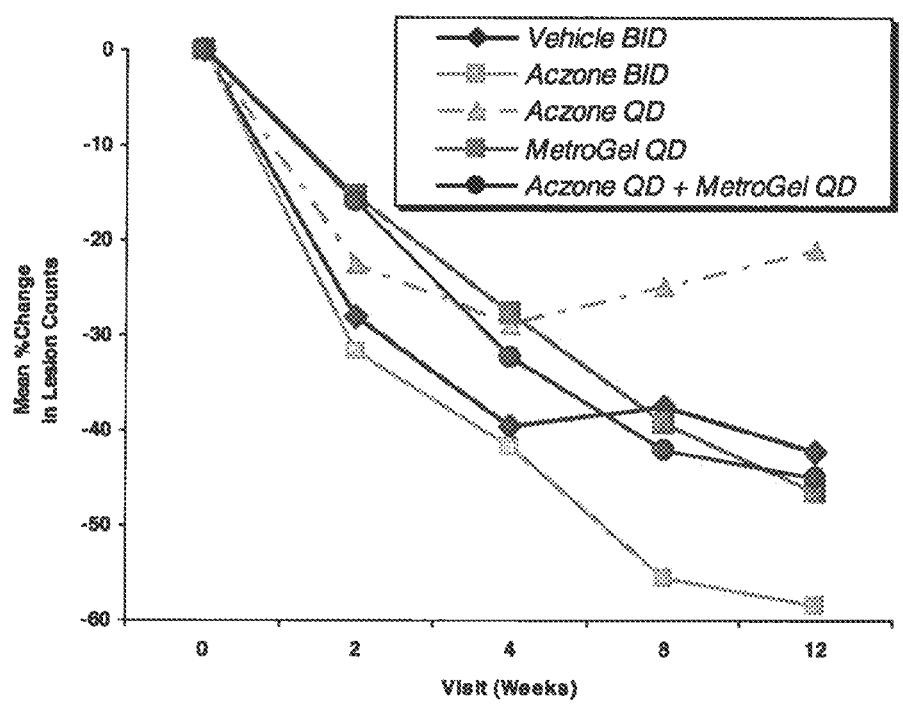
FIG. 6 shows mean percent change from baseline in inflammatory lesion counts for subjects with ≥20 lesions.

FIG. 6 shows the mean percent change from baseline in inflammatory lesion counts in the subgroup population having ≥20 inflammatory lesions (papules and/or pustules) above the mandibular line. All study treatment groups experienced a mean percent decrease from baseline in lesion counts. Diamonds, vehicle control; light squares, Aczone™ (dapsone 5%) 2×/day; triangles, Aczone™ (dapsone 5%) 1×/day; dark squares, MetroGel® (metronidazole 1%) 1×/day; circles, Aczone™ 1×/day+MetroGel® 1×/day. At Week 12, subjects treated with dapsone 2×/day, MetroGel® 1×/day, and dapsone+MetroGel® experienced the largest mean percent decreases from baseline (58.4%, 46.6% and 45.0% reduction in lesions, respectively) while subjects in the dapsone 1×/day group experienced the least mean percent decrease from baseline (20.9% decrease in lesions from baseline). The mean percent change from baseline in the vehicle control group was 42.3%.

IGA Success.

The IGA score and success rate from the IGA were summarized by frequencies and percents. Success rate was defined as the proportion of subjects with a score of 0 (clear) or 1 (almost clear) and at least a 2 point improvement from baseline on the 5-point Investigator's Global Assessment (IGA) scale of disease severity. In addition, 95% confidence intervals were calculated for the success rate from the IGA for each treatment group and for the difference between VC and each active treatment group.

Figure 7:
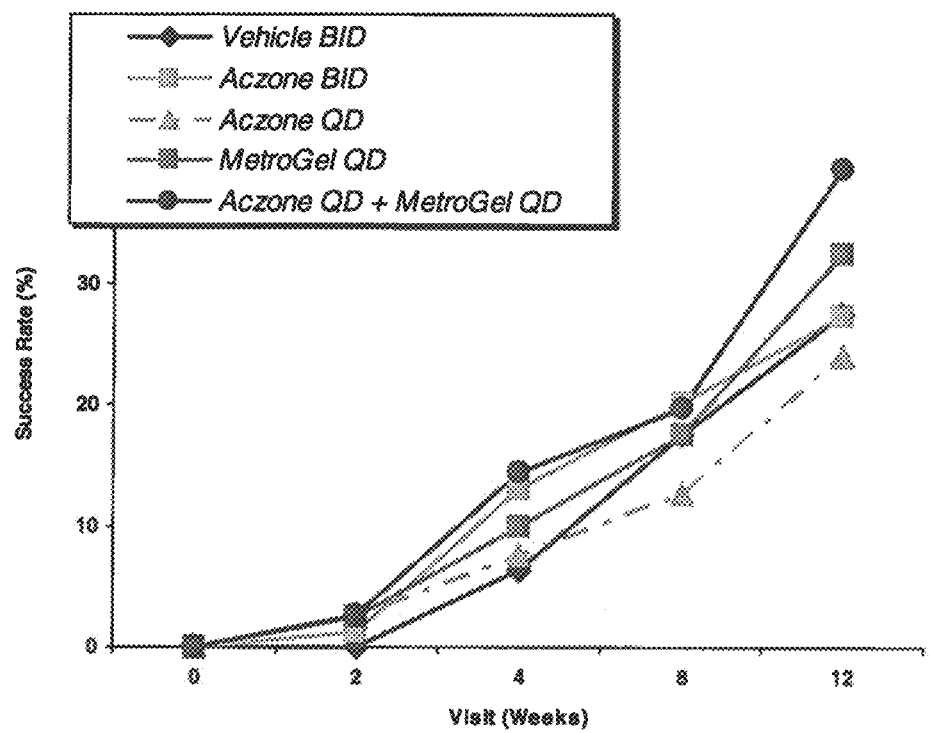
FIG. 7 shows the Investigator's Global Assessment (IGA) success rate over the course of the study in the intent to treat (ITT) population having ≥10 inflammatory lesions.
Figure 8:
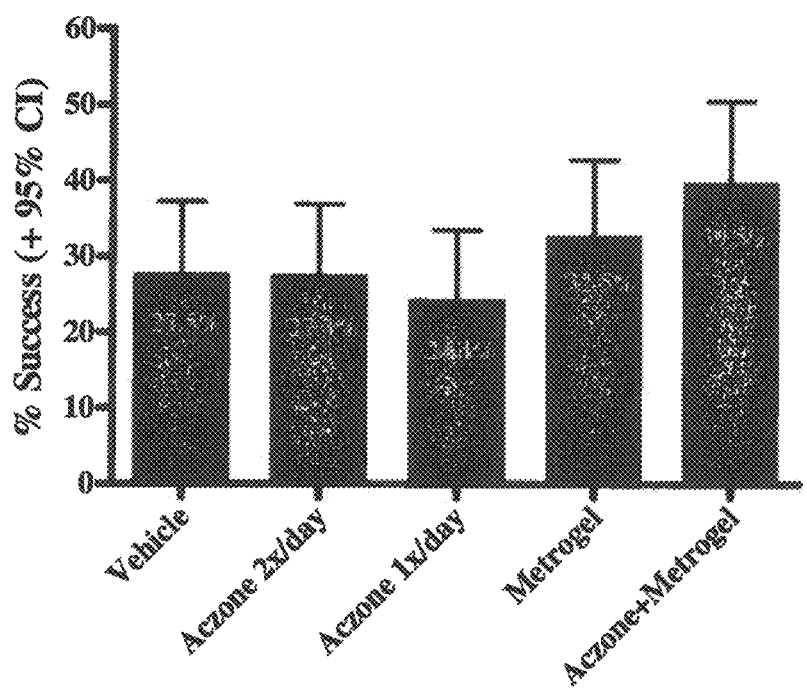
FIG. 8 summarizes the Investigator's Global Assessment (IGA) success rate at week 12 in the intent to treat (ITT) population having ≥10 inflammatory lesions.

At baseline, most subjects had an IGA score of moderate (62% for all subjects combined). The distribution of IGA scores shifted towards improvement as early as Week 2 for all study treatments, where the percentages of subjects with scores of moderate or severe decreased and percentages of subjects with scores of mild or almost clear increased. FIG. 7 shows the IGA success rate over the course of the study in the intent to treat (ITT) population having ≥10 inflammatory lesions. At Week 12, approximately one third to one half of the subjects enrolled in each group had an IGA score of clear (5.1% to 19.7%) or almost clear (25.0% to 33.8%). Diamonds, vehicle control; light squares, Aczone™ (dapsone 5%) 2×/day; triangles, Aczone™ (dapsone 5%) 1×/day; dark squares, MetroGel® (metronidazole 1%) 1×/day; circles, Aczone™ 1×/day+MetroGel® 1×/day. FIG. 8 summarizes the IGA success rate at week 12 in the intent to treat (ITT) population having ≥10 inflammatory lesions. At 12 weeks, the success rate was highest in the dapsone+MetroGel® group (39.5%) and lowest in the dapsone 1×/day group (24.1%). The success rate in the dapsone 2×/day group was higher than the dapsone 1×/day group but the rate was very similar to VC (27.4% and 27.5%, respectively). The combination treatment group experienced higher success than either the MetroGel® alone (32.5%) or the dapsone 1×/day (24.1%).

Subgroup Analysis: Subjects with <20 Lesions.

Figure 9:
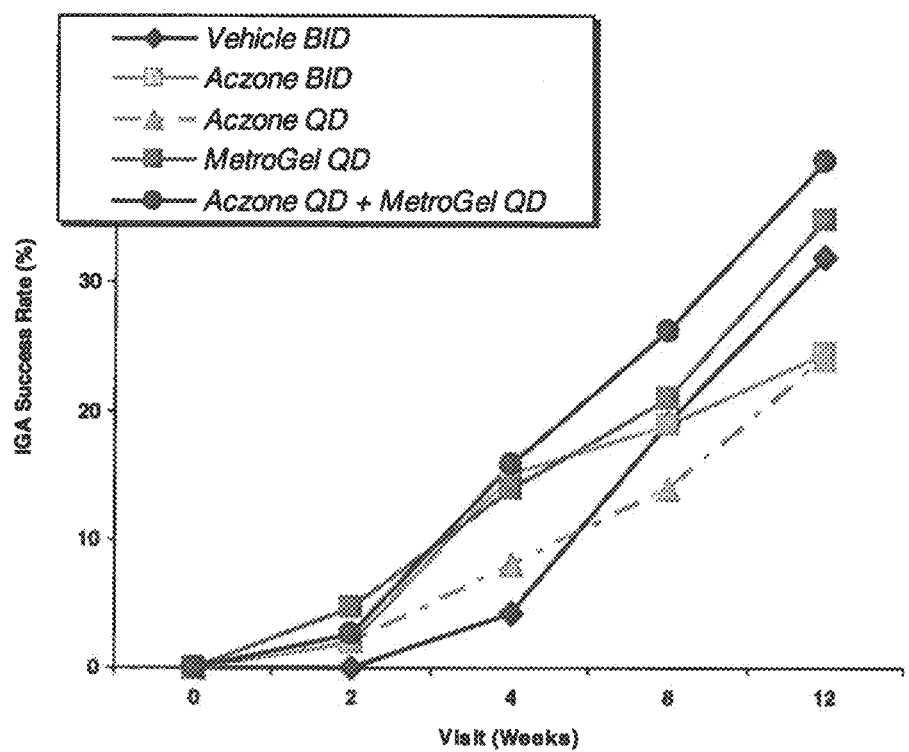
FIG. 9 shows the Investigator's Global Assessment (IGA) success rate over the course of the study in subjects with <20 inflammatory lesions.

At baseline, 56% of the subjects with <20 lesions had a moderate score on the IGA, while 41% had a mild score on the IGA. The distribution of IGA scores in subjects with <20 lesions at baseline shifted towards improvement over the 12 weeks for all study treatments. FIG. 9 shows the IGA success rate over the course of the study in subjects with <20 lesions. Diamonds, vehicle control; light squares, Aczone™ (dapsone 5%) 2×/day; triangles, Aczone™ (dapsone 5%) 1×/day; dark squares, MetroGel® (metronidazole 1%) 1×/day; circles, Aczone™ 1×/day+MetroGel® 1×/day. At week 12, approximately 40% to 60% of the subjects enrolled in each group had an IGA score of clear (4.0% to 26.3%) or almost clear (29.8% to 42.0%).

Subgroup Analysis: Subjects with ≥20 Lesions.

Figure 10:
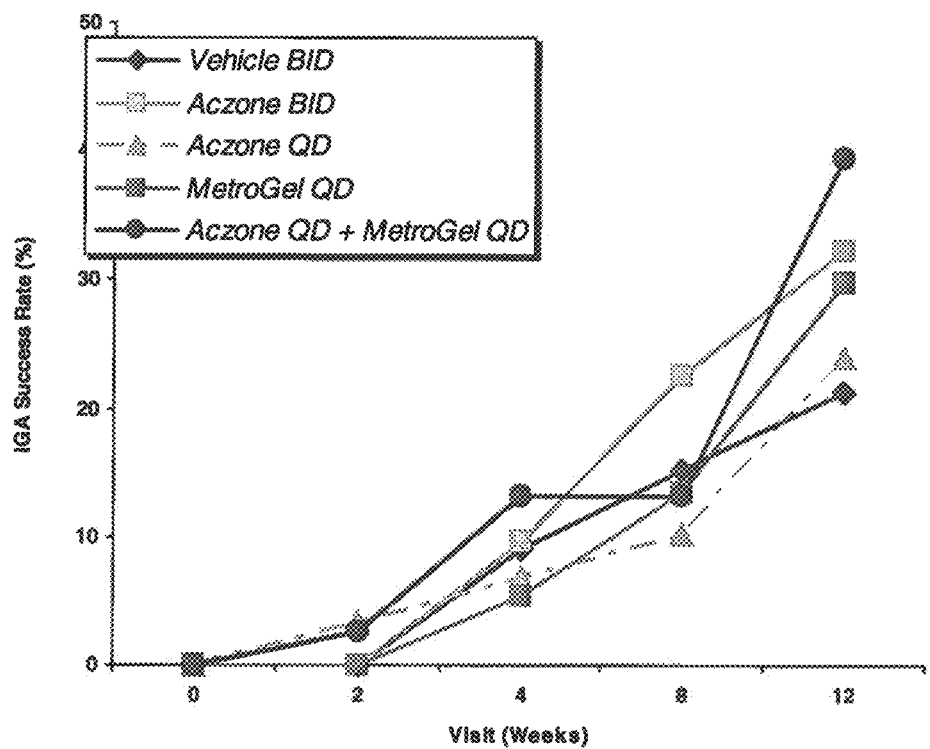
FIG. 10 shows the Investigator's Global Assessment (IGA) success rate over the course of the study in subjects with ≥20 lesions.

At baseline, most subjects with ≥20 lesions had a moderate score on the IGA (70%). Similar to the ITT analysis, the distribution of IGA scores in subjects with ≥20 lesions at baseline shifted towards improvement as early as Week 2 for all study treatments, where the percentages of subjects with scores of moderate or severe decreased and percentages of subjects with scores of mild or almost clear increased. FIG. 10 shows the IGA success rate over the course of the study in subjects with ≥20 lesions. At Week 12, approximately one third to one half of the subjects enrolled in each group had an IGA score of clear (6.5% to 13.2%) or almost clear (17.2% to 29.7%). Diamonds, vehicle control; light squares, Aczone™ (dapsone 5%) 2×/day; triangles, Aczone™ (dapsone 5%) 1×/day; dark squares, MetroGel® (metronidazole 1%) 1×/day; circles, Aczone™ 1×/day+MetroGel® 1×/day.

Figure 11:
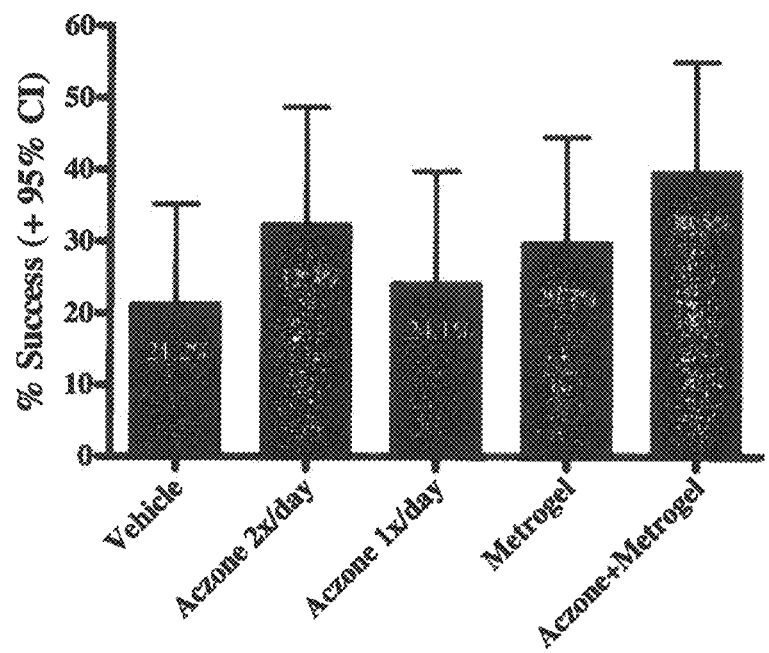
FIG. 11 summarizes the Investigator's Global Assessment (IGA) success rate at week 12 for the subgroup of subjects with ≥20 lesions.

FIG. 11 summarizes the IGA success rate for this subgroup at week 12. The percentage of subjects with ≥20 lesions who had treatment success at Week 12 was highest in the dapsone+MetroGel® group (39.5%) and lowest in the VC group (21.2%). Success rates were better in the dapsone 2×/day group (32.3%) than either the dapsone 1×/day group (24.1%) or the VC (21.2%), equivalent to an 11.1% difference favoring dapsone 2×/day treatment. Comparing the dapsone+MetroGel® group to the MetroGel® alone group, there was a higher success rate for the combination treatment (39.5% compared to 29.7%).

Erythema Assessment.

Erythema assessment scores were summarized by frequencies and percents. Erythema was graded according to the standardized scale shown in Table 2, at Day 0 (baseline) and Weeks 2, 4, 8, and 12.

TABLE 2

Erythema Assessment

| Score | Severity | Description |
|---|---|---|
| 0 | Absent | No perceptible erythema. |
| 1 | Mild | Slight erythema with either restricted central involvement or generalized whole face. |
| 2 | Moderate | Pronounced erythema with either restricted central involvement or generalized whole face. |
| 3 | Severe | Severe erythema or red-purple hue with either restricted central involvement or generalized whole face. |

At baseline, all subjects had at least mild erythema present (16.5% to 23.8%) with the majority displaying moderate erythema (60.0% to 70.9%). In general, erythema scores improved throughout the study, with 4.8% to 9.2% of subjects exhibiting no erythema at Week 12. There were no consistent differences in the distribution of erythema scores across study treatment groups.

Subgroup Analysis: Subjects with ≥20 Lesions.

For the subgroup of subjects with ≥20 lesions, erythema was predominantly moderate at baseline. The distribution of erythema scores tended to shift towards improvement as the study progressed in all treatment groups. By Week 12, approximately half of the subjects in each group had improved to a score of absent (3.2% to 9.1%) or mild (31.6% to 51.4%) from mostly moderate at baseline (58.1% to 82.8%). There were no consistent differences between the treatment groups.

Telangiectasia Assessment.

Telangiectasia assessment scores were summarized by frequencies and percents. Telangiectasia was graded according to the standardized scale shown in Table 3 at Day 0 (baseline) and Weeks 2, 4, 8, and 12.

TABLE 3

Telangiectasia Assessment

| Score | Severity | Description |
|---|---|---|
| 0 | Absent | No perceptible telangiectasia. |
| 1 | Mild | Involvement of the nose. |
| 2 | Moderate | Involvement of the nose and infraorbital region. |
| 3 | Severe | Involvement of the nose, infraorbital region, and other areas of the face. |

At baseline, telangiectasia was predominantly moderate (41.7% to 57.5% of subjects). Throughout the study, there was a small shift towards improvement of telangiectasia, demonstrated by an increase in the percentages of subjects with absent or mild telangiectasia and decreases in the percentages of subjects with moderate or severe telangiectasia. At Week 12, approximately half of the subjects in each group had either absent (13.1% to 19.7%) or mild telangiectasia (34.2% to 43.8%). There were no consistent differences in the distribution of telangiectasia scores across study treatment groups.

Subgroup Analysis Subjects with ≥20 Lesions.

At baseline, the telangiectasia score was predominantly mild in subjects with ≥20 lesions in the dapsone 2×/day group (51.6%) and moderate (48.3% to 63.6%) for other treatments. This pattern was still evident at Week 12; however the percentages of subjects with moderate or severe telangiectasia generally decreased while the percentages of subjects with mild or absent generally increased.

Adverse Events.

Application site adverse events were the most common type of adverse event reported. The majority of application site adverse events (dryness, itching, stinging, and burning) are signs and symptoms of rosacea that were solicited and scored using the standardized grading system shown in Table 4.

TABLE 4

Local Symptoms Assessment (Dryness, Itching, Stinging, and Burning)

| Score | Severity | Description |
|---|---|---|
| 0 | Absent | None |
| 1 | Mild | Barely perceptible |
| 2 | Moderate | Definitely present |
| 3 | Severe | Marked, intense |

The most frequent application site adverse event was dryness, which occurred at a similar frequency among study treatment groups (32.5% to 36.7%) and was typically mild to moderate in intensity. Other application site adverse events were pain (8.0% to 29.1%), burning (10.7% to 27.8%), pruritus (8.0% to 22.8%), and erythema (9.1% to 13.9%). The frequency of these application site adverse events was numerically lower in groups treated with MetroGel® alone or MetroGel®+dapsone compared with the vehicle control or dapsone-only treated groups. For all groups, the intensity of application site pain, burning, and pruritus was mostly mild while the intensity of application site erythema was mostly moderate to severe. The higher severity of application site erythema compared with other signs/symptoms of rosacea may be explained by the presence of erythema at baseline (which was mostly moderate) as part of the underlying rosacea characteristics whereas other local signs and symptoms were mostly absent or mild.

Skin and Subcutaneous Disorders occurred at a frequency ranging from 12.0% to 20.8%. The frequency was higher in the MetroGel® group (20.8%) compared with other groups (12.0% to 17.7%). Telangiectasia, reported as a worsening of baseline telangiectasia that was part of the subject's underlying rosacea, was the only adverse event to occur with a frequency higher than 1% (10.8% to 14.3%). The incidence of telangiectasia was slightly higher in groups treated with MetroGel® or MetroGel®+dapsone than the vehicle or dapsone-only treated group.

The amounts of dapsone and metabolites N-acetyl dapsone and N-hydroxylamine dapsone in plasma were measured at baseline, Week 2, Week 4, and Week 12 of the study. Mean plasma concentrations of dapsone and metabolites were low in study treatment groups using Aczone™ at all time points measured in the study. The highest mean plasma concentrations were observed at Week 2, where subjects had a mean dapsone concentration of 10.6 ng/mL, 7.0 ng/mL, and 6.1 ng/mL in the Aczone™ 2×/day group, Aczone™ 1×/day group, and Aczone™+MetroGel® group, respectively. The maximum plasma concentration of dapsone observed in any subject was 87.43 ng/mL, at Week 2

(Aczone™ 2x/day group). Plasma concentrations of N-acetyl dapsone were also highest at Week 2 (means of 4.9, 3.1, and 2.9 ng/mL in the Aczone™ 2x/day, Aczone™ 1x/day, and combination groups respectively). Plasma concentrations of the hydroxylamine metabolite, which is believed to be the primary factor associated with dapsone hematological toxicities, were much lower than the parent (mean values<1 ng/mL in all Aczone™-treated groups, maximum in any subject using Aczone™ 2x/day was 6.7 ng/mL).

In subjects treated with the combination of Aczone™ and MetroGel, plasma levels of dapsone and metabolites were similar to or lower than subjects treated with the same amount of Aczone™ only (1x/day), suggesting that there are no pharmacokinetic interactions between these two drugs.

Subjects with G6PD-deficiency are known to be at higher risk of developing dapsone-related hematological toxicities following oral dapsone use. In this study, 1 subject with G6PD-deficiency was enrolled and treated with Aczone™ (1x/day). When measured at Weeks 2, 4, and 12, the subject's plasma dapsone levels were approximately 11 to 12 ng/mL and hydroxylamine levels<1 ng/mL. The subject's laboratory data does not reveal any changes from baseline over the course of the study, except for slightly elevated non-fasting blood glucose at Week 4 and slightly low monocyte counts at Weeks 2 and 4 that were not deemed to be clinically significant. There were no changes in any hematological parameters. Furthermore, there were no adverse events reported indicative of systemic dapsone toxicity; only mild, transient application site adverse events were reported by this subject.

Systemic exposure to dapsone and its metabolites was low at all time points in the study. Similar mean values for hemoglobin, hematocrit, red blood cells, mean corpuscular volume, mean corpuscular hemoglobin, reticulocyte count, total bilirubin, haptoglobin, and LDH between baseline and Week 12 were shown across all treatment groups. There were no overall changes in any chemistry or hematology parameter observed during the study. These findings demonstrate the low incidence of systemic adverse events with topical dapsone use and support the safety of using topical dapsone, as well as dapsone in combination with Metro-Gel®, in subjects with papulopustular rosacea.

Discussion

The efficacy of dapsone in treating subjects with papulopustular rosacea was investigated. Two dapsone-alone dosage regimens (1x/day and 2x/day) were employed, as was a dapsone+MetroGel® regimen (1x/day). The study was controlled with the dapsone vehicle applied 2x/day (VC) and with MetroGel® alone (applied 1x/day).

Baseline characteristics were generally similar across study treatment groups, except the percentage of patients who had severe telangiectasia at baseline was more variable (6% in the Vehicle and MetroGel® groups, 20% and 15% in the dapsone 2x/day and 1x/day respectively, and 17% in the dapsone+MetroGel® group).

All treatment groups experienced a mean decrease from baseline in lesion counts. At Week 12, subjects treated with MetroGel® alone or dapsone+MetroGel® experienced the largest mean decreases from baseline in lesion counts (−11.3 and −11.4 lesions, respectively) while subjects in the dapsone 1x/day group experienced the least mean decrease from baseline (−5.7 lesions). The mean change from baseline in the dapsone 2x/day group (−8.0 lesions) was higher than the dapsone 1x/day group, but similar to the vehicle control (VC) group (−8.3 lesions).

Success rates, defined as a score of clear or almost clear with at least 2 points of improvement on a 5-point IGA scale, showed that more subjects treated with dapsone 2x/day had success (27.4%) than subjects treated with dapsone 1x/day (24.1%), but there was no difference from VC (27.5%). The success rate for the combination treatment of dapsone+MetroGel® was higher than MetroGel® alone (39.5% success rate compared with 32.5%).

Erythema and telangiectasia were evaluated, using a standardized 4-point grading system. Both erythema and telangiectasia improved, though not substantially, in all study treatment groups by Week 12. There were no apparent differences in erythema and telangiectasia between treatment groups.

Subgroup Analysis: Subjects with ≥20 Lesions at Baseline.

Subjects with ≥20 lesions in all treatment groups experienced a greater mean decrease from baseline in inflammatory lesion count than the overall mean decrease for the ITT population having ≥10 inflammatory lesions and the subgroup having <20 inflammatory lesions. This result was surprising because a milder form of the disease would be expected to show similar or improved treatment results compared to a more severe form of the disease. In this subgroup of subjects with ≥20 lesions, the dapsone 2x/day, MetroGel®, and dapsone+MetroGel® groups experienced the highest mean decreases by Week 12 (−15.5, −15.5, and −15.6 lesions respectively, corresponding to 58.4%, 46.6% and 45.0% reductions from baseline in lesions, respectively). The VC group experienced a mean decrease of −11.6 lesions (a 42.3% decrease) and the dapsone 1x/day group experienced a mean decrease of −9.3 lesions (a 20.9% decrease in lesions from baseline) at 12 weeks. Comparing the dapsone 2x/day and VC groups, there was a 3.9 lesion difference in the mean decrease from baseline in favor of dapsone.

In the ≥20 lesions subgroup, success at Week 12 was highest in the dapsone+MetroGel® group (39.5%) and lowest in the VC group (21.2%). Success rates were better in the dapsone 2x/day group (32.3%) than either the dapsone 1x/day group (24.1%) or the VC group (21.2%), equivalent to an 11.1% difference favoring dapsone 2x/day treatment. Comparing the dapsone+MetroGel® group to the MetroGel® alone group, there was a higher success rate for the combination treatment (39.5% compared to 29.7%).

Systemic exposure to dapsone and its metabolites was low at all time points in the study. Treatment with dapsone was safe and well tolerated in subjects with papulopustular rosacea. Most adverse events were at the application site, were mild, and were transient. Systemic adverse events were infrequent and were generally indicative of the common cold or flu. The most frequent adverse events were application site events including dryness, pain, burning, pruritus, and erythema, which are also known signs and symptoms of rosacea.

REFERENCES

1. Bikowski J B, Goldman M P. Rosacea: where are we now? J Drugs Dermatol. 2004 May-June; 3(3):251-61.
2. Bormann G, Gaber M, Fischer M, and Marsch W C. Dapsone in Rosacea Fulminans. J Eur Acad Derm. 2001; 15:465-467.
3. Borne P. Rosacea with special reference to its ocular manifestations. Br J. Ophthalmol. 1953; 65:458.
4. Bose S K. Association of Melkersson-Rosenthal Syndrome with Rosacea. J. Derm. 1996; 23:902-904.

5. Buechner S A. Rosacea: an update. Dermatology. 2005; 210(2):100-8.
6. Coleman M D, Pahal K K, Gardiner J M. The effect of acetylation and deacetylation on the disposition of dapsone and monoacetyl dapsone hydroxylamines in human erythrocytes in-vitro. J Pharm Pharmacol. 1996 April; 48(4):401-6.
7. Coleman M D, Smith J K, Penis A D, Buck N S, Seydel J K. Studies on the inhibitory effects of analogues of dapsone on neutrophil function in-vitro. J Pharm Pharmacol. 1997 January; 49(1):53-7.
8. Dahl, M V. Rosacea subtypes: a treatment algorithm. Cutis. 2004; 74 (suppl 3):21-27.
9. DeGowin R L. A review of therapeutic and hemolytic effects of dapsone. Arch Intern Med. 1967 August; 120 (2):242-8.
10. Del Rosso J Q, Wolf J E, Jr., Leyden J, Millikan L E, Odom R B, Shalita A. The treatment of rosacea. Cutis. 2004; 73 (1 Suppl):34-6.
11. Finacea® (azelaic acid gel), 15%. Package Insert. Intendix, May 2005.
12. Jenkins M A, Brown S I, Lempert S L, et al. Ocular rosacea. Am J. Ophthalmol. 1979; 88:618-622.
13. Jollow D J, Bradshaw T P, McMillan D C. Dapsone-induced hemolytic anemia. Drug Metab Review. 1995; 27:107-124.
14. Khokhar O, Khachemoune A. A case of granulomatous rosacea: sorting granulomatous rosacea from other granulomatous diseases that affect the face. Dermatol Online J. 2004 Jul. 15; 10(1):6.
15. Krause M H, Torricelli R, Kundig T, Trueb R M, Hafner J. Dapsone in granulomatous rosacea [in German]. Der Hautarzt. 1997; 48(4):246-248.
16. MetroGel® (metronidazole gel), 1.0%. Package Insert. Galderma Laboratories, June 2005.
17. Nase G. New Rosacea Treatments Offer Hope to Rosacea Sufferers. Dermatology Times, Aug. 1, 2005 (found at http://www.drnase.com/articles_future_treatments.htm)
18. Oracea™ (doxycycline, USP capsules), 40 mg. Package Insert. CollaGenex. May 2006.
19. Pelle M T. Rosacea therapy update. Adv Dermatol. 2003; 19:139-170.
20. Prendiville J S, Logan R A, Russell-Jones R. A comparison of dapsone with 13-cis retinoic acid in the treatment of nodular cystic acne. Clin Exp Dermatol. 1988; 13:67-71.
21. Ross C M. The treatment of acne vulgaris with dapsone. Br J. Dermatol. 1961 October; 73:367-70.
22. Shalita A, Leyden J. Mechanism-based selection of pharmacologic agents for rosacea. Cutis. 2004; 73 (1 Suppl):15-18.
23. Sibenge S and Gawkrodger D J. Rosacea: a study of clinical patterns, blood flow, and the role of *Demodex folliculorum*. J Am Acad Dermatol. 1992; 26:590-593.
24. Starr P A H, McDonald A. Oculocutaneous aspects of rosacea. Proc R Soc Med. 1969; 62:9.
25. Stone D U, Chodosh J. Ocular rosacea: an update on pathogenesis and therapy. 1: Curr Opin Ophthalmol. 2004 December; 15(6):499-502.
26. Thiboutot D, Thieroff-Ekerdt R, Graupe K. Efficacy and safety of azelaic acid (15%) gel as a new treatment for papulopustular rosacea: results from two vehicle-controlled, randomized phase III studies. J Am Acad Dermatol. 2003; 48(6):836-45.
27. Wilkin J, Dahl M, Detmar M, et al. Standard classification of rosacea: report of the national rosacea society expert committee on the classification and staging of rosacea. J Am Acad Dermatol. 2002; 46(4):584-7.
28. Wilkin J, Dahl M, Detmar M, et al. Standard grading system for rosacea: report of the national rosacea society expert committee on the classification and staging of rosacea. J Am Acad Dermatol. 2004; 50(6):907-912.
29. Zhu Y I, Stiller M J. Dapsone and sulfones in dermatology: overview and update. J Am Acad Dermatol. 2001; 45:420-34.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to treat mild to severe papulopustular rosacea comprising topically administering to a patient in need thereof an effective amount of a first pharmaceutical composition comprising dapsone and a pharmaceutically acceptable carrier, wherein said first pharmaceutical composition is a semisolid aqueous gel;
   wherein the pharmaceutical composition is administered twice daily; and
   wherein said method further comprises administering a second composition comprising metronidazole and a pharmaceutically acceptable carrier.

2. The method of claim 1 wherein the patient has an Investigator Global Assessment score of 3 or higher before treatment.

3. The method of claim 1 wherein treatment results in a mean reduction of at least 13 papulopustular lesions.

4. The method of claim 1 wherein treatment results in a mean reduction of at least 43% of the papulopustular lesions.

5. The method of claim 1 wherein the patient has 20 or more inflammatory lesions.

6. The method of claim 1 wherein the first pharmaceutical composition additionally comprises a thickening agent, a high-boiling, nonionic organic solvent, a preservative, or a base agent.

7. The method of claim 1 wherein the dapsone comprises about 0.5 wt % to 10 wt % of the pharmaceutical composition.

8. The method of claim 1 wherein the dapsone is present in both a microparticulate state and a dissolved state.

9. The method of claim 8 wherein the microparticulate dapsone is a crystalline precipitate.

10. The method of claim 8 wherein the microparticulate dapsone is an amorphous precipitate.

11. The method of claim 1 wherein the pharmaceutical composition further comprises an antioxidant, a fragrance, a colorant, a sunscreen, or combinations thereof.

12. The method of claim 1 wherein the pharmaceutical composition comprises about 5 wt % dapsone, about 0.85 wt % carbomer 980, about 25 wt % diethylene glycol monoethyl ether (DGME), about 0.2 wt % methylparaben, about 0.2 wt % sodium hydroxide; and about 68.75 wt % purified water.

* * * * *